(12) United States Patent
Wu et al.

(10) Patent No.: US 12,173,077 B2
(45) Date of Patent: Dec. 24, 2024

(54) HUMANIZED BCMA ANTIBODY AND BCMA-CAR-T CELLS

(71) Applicants: ProMab Biotechnologies, Inc., Richmond, CA (US); Forevertek Biotechnology Co., Ltd, Changsha (CN)

(72) Inventors: Lijun Wu, Berkeley, CA (US); Vita Golubovskaya, Pinole, CA (US)

(73) Assignees: ProMab Biotechnologies, Inc., Richmond, CA (US); Forevertek Biotechnology Co., Ltd, Changsha (CN)

( * ) Notice: Subject to any disclaimer, the term of this patent is extended or adjusted under 35 U.S.C. 154(b) by 0 days.

(21) Appl. No.: 18/326,826

(22) Filed: May 31, 2023

(65) Prior Publication Data

US 2023/0383002 A1    Nov. 30, 2023

Related U.S. Application Data

(60) Provisional application No. 63/365,562, filed on May 31, 2022.

(51) Int. Cl.
| | |
|---|---|
| *C07K 16/28* | (2006.01) |
| *C07K 14/725* | (2006.01) |
| *C12N 5/078* | (2010.01) |
| *A61K 39/00* | (2006.01) |

(52) U.S. Cl.
CPC ...... *C07K 16/2878* (2013.01); *C07K 14/7051* (2013.01); *C12N 5/0634* (2013.01); *A61K 39/4631* (2023.05); *C07K 2317/622* (2013.01); *C07K 2319/03* (2013.01)

(58) Field of Classification Search
CPC ............ C07K 16/2878; C07K 14/7051; C12N 5/00634; A61K 39/4631
See application file for complete search history.

(56) References Cited

U.S. PATENT DOCUMENTS

2014/0242701 A1 *  8/2014  Shiku ................. A61P 35/00
                                                                        435/325

FOREIGN PATENT DOCUMENTS

WO    WO-2020087054 A1 *  4/2020  ......... C07K 14/7151
WO    WO-2023109257 A1 *  6/2023

OTHER PUBLICATIONS

Wall et Al., Theriogenology, vol. 45, p. 57-68, 1996 (Year: 1996).*
Houdebine et Al., Journal of Biotechnology, vol. 34, p. 269-287, 1994 (Year: 1994).*
Houdebine (Comparative Immunology, Microbiology, and Infectious Diseases, vol. 32, p. 107-121, 2009) (Year: 2009).*
Kappell et Al., Current Opinions in Biotechnology, vol. 3, p. 548-553, 1992) (Year: 1992).*

* cited by examiner

*Primary Examiner* — Samira J Jean-Louis
*Assistant Examiner* — Latia D Saine
(74) *Attorney, Agent, or Firm* — Perkins Coie LLP; Viola Kung

(57) ABSTRACT

The present invention is directed to a humanized BCMA antibody or an antigen-binding fragment thereof, comprising $V_H$ having the amino acid sequence of SEQ ID NO: 3 and $V_L$ having the amino acid sequence of SEQ ID NO: 5. The present invention is also directed to a BCMA chimeric antigen receptor fusion protein comprising from N-terminus to C-terminus: (i) a single-chain variable fragment (scFv) of the present invention, (ii) a transmembrane domain, (iii) at least one co-stimulatory domains, and (iv) an activating domain. This humanized BCMA-CAR-T cells have specific killing activity against BCMA-positive tumor cells.

1 Claim, 19 Drawing Sheets
Specification includes a Sequence Listing.

```
         10         20         30         40         50
MLQMAGQCSQ NEYFDSLLHA CIPCQLRCSS NTPPLTCQRY CNASVTNSVK
         60         70         80         90        100
GTNAILWTCL GLSLIISLAV FVLMFLLRKI NSEPLKDEFK NTGSGLLGMA
        110        120        130        140        150
NIDLEKSRTG DEIILPRGLE YTVEECTCED CIKSKPKVDS DHCFPLPAME
        160        170        180
EGATILVTTK TNDYCKSLPA ALSATEIEKS ISAR
```

HUMANIZED BCMA ANTIBODY AND BCMA-CAR-T CELLS

This application claims priority to U.S. Provisional Application No. 63/365,562, filed May 31, 2022; the contents of which is incorporated herein by reference in its entirety.

REFERENCE TO SEQUENCE LISTING, TABLE OR COMPUTER PROGRAM

This application contains an ST.26 compliant Sequence Listing, which is submitted concurrently in xml format via Patent Center and is hereby incorporated by reference in its entirety. The .xml copy, created on May 31, 2023, is named Sequence Listing.xml and is 20,600 bytes in size.

FIELD OF THE INVENTION

The present invention relates to humanized BCMA antibody or an antigen-binding fragment therefore, and BCMA-CAR-T cells specifically decreasing multiple myeloma tumor growth, which are useful in the field of adoptive immunity gene therapy for tumors.

BACKGROUND OF THE INVENTION

Immunotherapy is emerging as a highly promising approach for the treatment of cancer. T cells or T lymphocytes, the armed forces of our immune system, constantly look for foreign antigens and discriminate abnormal (cancer or infected cells) from normal cells. Genetically modifying T cells with CAR (Chimeric antigen receptor) constructs is the most common approach to design tumor-specific T cells. CAR-T cells targeting tumor-associated antigens (TAA) can be infused into patients (called adoptive cell transfer or ACT) representing an efficient immunotherapy approach [1, 2]. The advantage of CAR-T technology compared with chemotherapy or antibody is that reprogrammed engineered T cells can proliferate and persist in the patient ("a living drug") [1, 2].

CARs typically consist of a monoclonal antibody-derived single-chain variable fragment (scFv) at the N-terminal part, hinge, transmembrane domain and a number of intracellular co-activation domains: (i) CD28, (ii) CD137 (4-1BB), CD27, or other co-stimulatory domains, in tandem with an activation CD3-zeta domain (FIG. 1). The evolution of CARs went from first generation (with no co-stimulation domains) to second generation (with one co-stimulation domain) to third generation CAR (with several co-stimulation domains). Generating CARs with two costimulatory domains (the so-called 3rd generation CAR) have led to increased cytolytic CAR-T cell activity, improved persistence of CAR-T cells leading to its augmented antitumor activity.

BCMA

B cell maturation antigen (BCMA) is a cell surface receptor, also known as CD269 and tumor necrosis factor receptor superfamily member 17 (TNFRSF17), that is encoded by TNFRSF17 gene. This receptor is expressed mainly in mature B lymphocytes and in most cases overexpressed in multiple myeloma (MM) [4]. Current therapies to target BCMA in MM include monoclonal antibodies, bispecific antibodies and T cellular immunotherapies, CAR-T therapies [4, 5].

The human BCMA protein consists of 184 amino-acids: 1-54-extracellular domain; 55-77-transmembrane domain; 78-184-cytoplasmic domain. The amino-acid sequence of BCMA is shown on FIG. 2. BCMA lacks signaling peptide and resembles other receptors BAFF Receptor and transmembrane activator and cyclophilin ligand interactor and calcium modulator (TACI) [4]. These receptors play major role in B cell maturation and differentiation into plasma cells. Their ligands include BAFF and APRIL which expression is increase in MM patients [4].

BRIEF DESCRIPTION OF THE DRAWINGS

FIG. 4A shows CHO-BCMA target cells. on the right: From top to bottom: Mock CAR-T cells, T cells, target cells alone, and humanized CAR-T cells. FIG. 4B shows CHO target cells. From top to bottom on the right, Mock CAR-T cells, humanized BCMA CAR-T cells, T cells, and target cells alone.

DETAILED DESCRIPTION OF THE INVENTION

Definitions

Figures 1, 2:
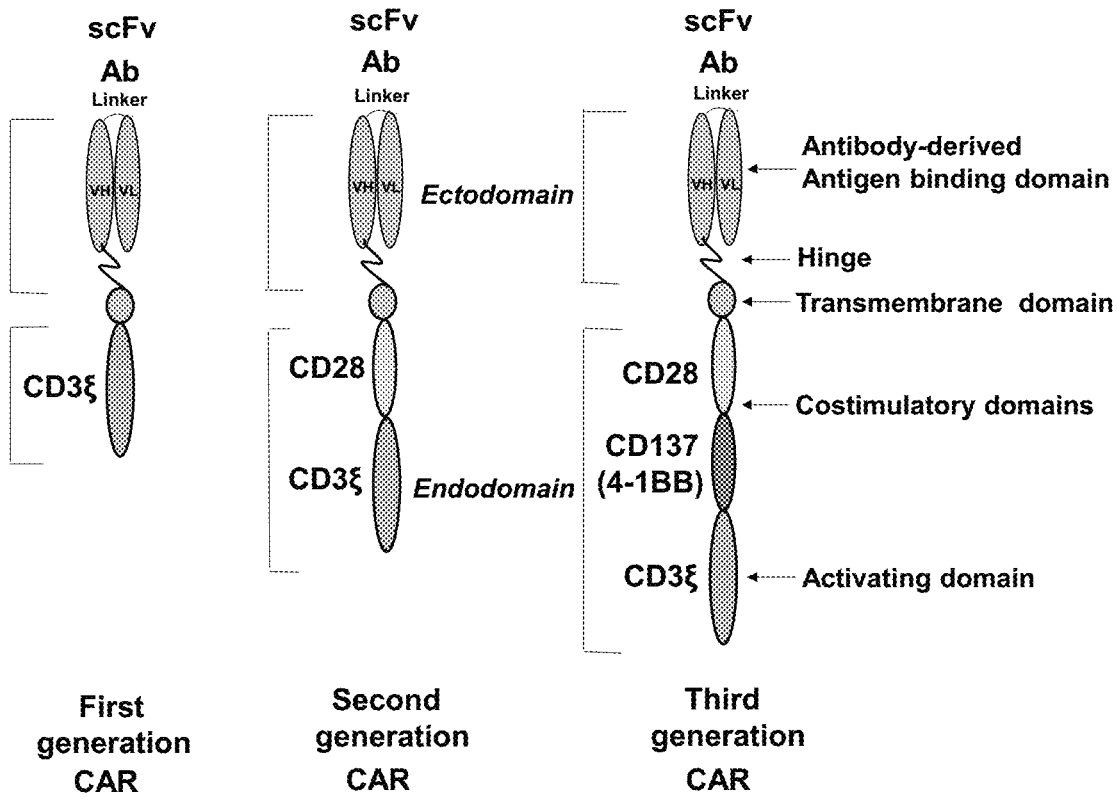
FIG. 1 shows the structures of CAR [3]. The left panel shows the structure of first generation (no costimulatory domains). The middle panel shows the structure of the second generation (one co-stimulation domain of CD28 or 4-BB). The right panel shows the structure of the third generation (two or more co-stimulation domains).
FIG. 2 shows the amino-acid sequence of BCMA protein (SEQ ID NO: 1). Extracellular domain is underlined.

As used herein, a "chimeric antigen receptor (CAR)" is a receptor protein that has been engineered to give T cells the new ability to target a specific protein. The receptor is chimeric because they combine both antigen-binding and T-cell activating functions into a single receptor. CAR is a fused protein comprising an extracellular domain capable of binding to an antigen, a transmembrane domain, and at least one intracellular domain. The "chimeric antigen receptor (CAR)" is sometimes called a "chimeric receptor", a "T-body", or a "chimeric immune receptor (CIR)." The "extracellular domain capable of binding to an antigen" means any oligopeptide or polypeptide that can bind to a certain antigen. The "intracellular domain" means any oligopeptide or polypeptide known to function as a domain that transmits a signal to cause activation or inhibition of a biological process in a cell.

As used herein, a "domain" means one region in a polypeptide which is folded into a particular structure independently of other regions.

As used herein, "humanized antibodies" are antibodies derived from non-human species whose protein sequences have been modified to increase their similarity to antibody variants produced naturally in humans. For example, after a mouse antibody is developed, the DNA coding for that antibody can be sequenced. The DNA sequence corresponding to the antibody CDRs can then be determined. The CDR sequences can be inserted into a construct containing the DNA for a human antibody variant to prepare humanized antibodies.

As used herein, a "single chain variable fragment (scFv)" means a single chain polypeptide derived from an antibody which retains the ability to bind to an antigen. An example of the scFv includes an antibody polypeptide which is formed by a recombinant DNA technique and in which Fv regions of immunoglobulin heavy chain (H chain) and light chain (L chain) fragments are linked via a spacer sequence. Various methods for engineering an scFv are known to a person skilled in the art.

As used herein, a "tumor antigen" means a biological molecule having antigenicity, expression of which causes cancer.

The inventors have engineered humanized BCMA scFv starting from heavy and light chain variable regions of mouse monoclonal antibody derived from a mouse monoclonal antibody, clone 4C8A. Mouse 4C8A antibody exhibits strong and selective binding to human BCMA [6].

The present invention provides a humanized monoclonal anti-human BCMA antibody (PM 307) or an antigen-binding fragment thereof, for example, Fab, Fab', F(ab')$_2$, Fv fragments, and single-chain variable fragment scFv, obtained by sequencing and humanizing mouse monoclonal anti-BMCA antibody (hybridoma clone 4C8A [6]). The humanized anti-human BCMA antibody comprises humanized VH having the amino acid sequence of SEQ ID NO: 3 and humanized VL having the amino acid sequence of SEQ ID NO: 5. In one embodiment, the present invention is directed to a humanized anti-human BCMA single-chain variable fragment (scFv). ScFv can be VH-linker-VL or VL-linker-VH.

The present invention is also directed to a chimeric antigen receptor fusion protein comprising from N-terminus to C-terminus: (i) a single-chain variable fragment (scFv) against BCMA in which $V_H$ has the amino acid sequence of SEQ ID NO: 3, and $V_L$ has the amino acid sequence of SEQ ID NO: 5, (ii) a transmembrane domain, (iii) at least one co-stimulatory domains, and (iv) an activating domain.

The inventors have produced BCMA-CAR-T cells based on humanized BCMA antibody to target cancer cells overexpressing BCMA tumor antigen. The BCMA-CAR-T cells of the present invention have high cytotoxic activity against several cancer cell lines.

Figure 3:
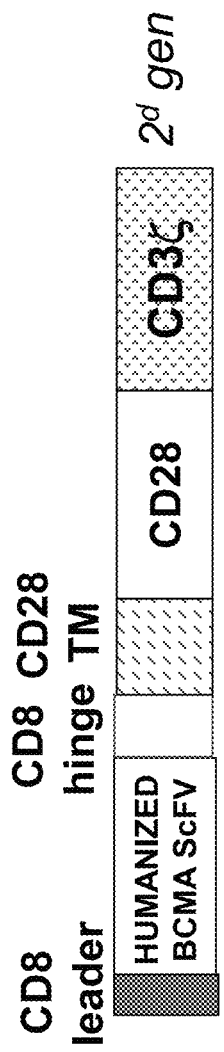
FIG. 3 shows the structure of humanized BCMA CAR construct.

In one embodiment, the CAR structure is shown in FIG. 3.

In one embodiment, the co-stimulatory domain is selected from the group consisting of CD28, 4-1BB, GITR, ICOS-1, CD27, OX-40 and DAP10. A preferred the co-stimulatory domain is CD28.

A preferred activating domain is CD3 zeta (CD3 Z or CD3ζ).

The transmembrane domain may be derived from a natural polypeptide, or may be artificially designed. The transmembrane domain derived from a natural polypeptide can be obtained from any membrane-binding or transmembrane protein. For example, a transmembrane domain of a T cell receptor α or β chain, a CD3 zeta chain, CD28, CD3ε, CD45, CD4, CD5, CD8, CD9, CD16, CD22, CD33, CD37, CD64, CD80, CD86, CD134, CD137, ICOS, CD154, or a GITR can be used. The artificially designed transmembrane domain is a polypeptide mainly comprising hydrophobic residues such as leucine and valine. It is preferable that a triplet of phenylalanine, tryptophan and valine is found at each end of the synthetic transmembrane domain. Optionally, a short oligopeptide linker or a polypeptide linker, for example, a linker having a length of 2 to 10 amino acids can be arranged between the transmembrane domain and the intracellular domain. In one embodiment, a linker sequence having a glycine-serine continuous sequence can be used.

The present invention provides a nucleic acid encoding the BCMA-CAR. The nucleic acid encoding the CAR can be prepared from an amino acid sequence of the specified CAR by a conventional method. A base sequence encoding an amino acid sequence can be obtained from NCBI RefSeq IDs or accession numbers of GenBank for an amino acid sequence of each domain, and the nucleic acid of the present invention can be prepared using a standard molecular biological and/or chemical procedure. For example, based on the base sequence, a nucleic acid can be synthesized, and the nucleic acid of the present invention can be prepared by combining DNA fragments which are obtained from a cDNA library using a polymerase chain reaction (PCR).

A nucleic acid encoding the CAR of the present invention can be inserted into a vector, and the vector can be introduced into a cell. For example, a virus vector such as a retrovirus vector (including an oncoretrovirus vector, a lentivirus vector, and a pseudo type vector), an adenovirus vector, an adeno-associated virus (AAV) vector, a simian virus vector, a vaccinia virus vector or a sendai virus vector, an Epstein-Barr virus (EBV) vector, and a HSV vector can be used. A virus vector lacking the replicating ability so as not to self-replicate in an infected cell is preferably used.

For example, when a retrovirus vector is used, a suitable packaging cell based on a LTR sequence and a packaging signal sequence possessed by the vector can be selected for preparing a retrovirus particle using the packaging cell. Examples of the packaging cell include PG13 (ATCC CRL-10686), PA317 (ATCC CRL-9078), GP+E-86 and GP+envAm-12, and Psi-Crip. A retrovirus particle can also be prepared using a 293 cell or a 293T cell having high transfection efficiency. Many kinds of retrovirus vectors produced based on retroviruses and packaging cells that can be used for packaging of the retrovirus vectors are widely commercially available from many companies.

A CAR-T cell binds to a specific antigen via the CAR, thereby a signal is transmitted into the cell, and as a result, the cell is activated. The activation of the cell expressing the CAR is varied depending on the kind of a host cell and an intracellular domain of the CAR, and can be confirmed based on, for example, release of a cytokine, improvement of a cell proliferation rate, change in a cell surface molecule, or the like as an index. For example, release of a cytotoxic cytokine (a tumor necrosis factor, lymphotoxin, etc.) from the activated cell causes destruction of a target cell expressing an antigen. In addition, release of a cytokine or change in a cell surface molecule stimulates other immune cells, for example, a B cell, a dendritic cell, a NK cell, and a macrophage.

The cell expressing the CAR can be used as a therapeutic agent for a disease. The therapeutic agent comprises the cell expressing the CAR as an active ingredient, and it may further comprise a suitable excipient.

The inventors have generated CAR-T cells based on humanized BCMA ScFv sequence specifically targeting BCMA. The inventors have produced humanized BCMA-CAR-T cells to target cancer cells overexpressing BCMA tumor antigen. The humanized BCMA-CAR-T cells of the present invention secreted high level of cytokines against multiple myeloma cancer cells and kill CHO-BCMA-positive target cells but not control parental CHO cells.

The advantages of the humanized BCMA-ScFv of the present invention over the corresponding mouse ScFv include less immunogenicity to human due to the humanized BCMA scFv sequence. Thus, the humanized BCMA antibody of the present invention is highly potent and advantageous as therapeutic agents in many clinical applications.

The present humanized BCMA ScFv can be used for immunotherapy applications: toxin/drug-conjugated antibody, monoclonal therapeutic antibody, and CAR-T cell immunotherapy.

Humanized BCMA-CAR-T cells using the present humanized BCMA ScFv effectively target BCMA antigen in BCMA-positive cancer cell lines such as ovarian, colon, pancreatic, melanoma, cervical cancer, and other BCMA-positive cancers.

Humanized BCMA-CAR-T cells can be used in combination with different chemotherapy: checkpoint inhibitors, targeted therapies, small molecule inhibitors, and antibodies.

Humanized BCMA-CAR-T cells can be used clinically for BCMA-positive cancer cells.

Modifications of co-activation domains such as CD28, 4-1BB and others can be used to increase the efficacy of CAR-T cells. Tag-conjugated humanized BCMA scFv can be used for CAR generation.

Humanized BCMA-CAR-T cells can be used with different safety switches such as t-EGFR, RQR (Rituximab-CD34-Rituximab), inducible caspase-9 and other.

Third generation CAR-T or other co-activation signaling domains can be used with humanized BCMA-scFv to prepare BCMA-CAR-T.

The humanized BCMA CAR can be combined with CARs targeting other tumor antigens or tumor microenvironment, e.g., VEGFR-1-3, PDL-1. Bi-specific antibodies against BCMA and CD3, or other antigens can be generated for therapy.

The humanized BCMA-CAR can be used for generating other types of cells such as CAR-natural killer (NK) cells, BCMA-CAR-macrophages, allogenic CAR-T cells, gene-edited T cells, and other BCMA-CAR hematopoietic cells, which can target BCMA-positive cancers.

The present invention provides T cells, NK cells, macrophages, or hematopoietic cells, modified to express BCMA-CAR.

BCMA-CAR-T cells can be used against cancer stem cells and circulating tumor stem cells that are most resistant against chemotherapy and form aggressive tumors.

BCMA-CAR-T cells, BCMA-NK cells, BCMA-macrophages, and other cells can be used for targeting different types of cancers.

BCMA-CAR-T cells can be delivered intratumorally to patients for increased safety.

The following examples further illustrate the present invention. These examples are intended merely to be illustrative of the present invention and are not to be construed as being limiting.

EXAMPLES

Example 1. Humanized BCMA VH and VL and scFv Sequences

The BCMA scFv was derived from hybridoma clone 4C8A (WO2019/195017), positive for BCMA. The sequences of heavy and light chain variable regions of mouse clone 4C8A were determined and used to construct a humanized scFv.

The structure of humanized BCMA (PMC307) scFv is: $V_H$-linker-$V_L$. Linker is G4Sx3 (SEQ ID NO: 4).

The nucleotide sequence of humanized BCMA PMC307 ScFv clone is shown below. $V_H$ is bolded, $V_L$ is underlined, in between (italicized) is the nucleotide sequence encoding a linker.

```
                                       (SEQ ID NO: 2)
caggtgcagctggtgcagagcggcgcggaagtgaaaaaac cggggcagcagcgtgaaagtgagctgcaaagcgagcggcta tacctttaccagctatgtgatgcattgggtgcgccaggcg ccggggccagggcctggaatggatgggctatattattccgt ataacgatgcgaccaaatatgcgcagaaatttcagggccg cgtgaccattaccgcggataaaagcaccagcaccgcgtat atggaactgagcagcctgcgcagcgaagataccgcggtgt attattgcgcgcgctataactatgatggctattttgatgt gtggggccagggcaccctggtgaccgtgagcagcggcggc ggcggcagcggcggcggcggcagcggcggcggcggcagcg aaattgtgctgacccagagcccggcgaccctgagcctgag cccgggcgaacgcgcgaccctgagctgccgcgcgagccag agcattagcgattatctgcattggtatcagcagaaaccgg gccaggcgccgcgcctgctgatttattatgcgagccagag cattaccggcattccggcgcgctttagcggcagcggcagc ggcaccgatttttaccctgaccattagcagcctggaaccgg aagattttgcggtgtattattgccagaacggccatagctt tccgccgacctttggcggcggcaccaaagtggaaattaaa
```

PMC307 $V_H$ amino acid sequence:

(SEQ ID NO: 3)

QVQLVQSGAEVKKPGSSVKVSCKASGYTFTSYVMHWVRQA

PGQGLEWMGYIIPYNDATKYAQKFQGRVTITADKSTSTAY

MELSSLRSEDTAVYYCARYNYDGYFDVWGQGTLVTVSS

Linker amino acid sequence (SEQ ID NO: 4)

GGGGSGGGGSGGGGS

PMC307 VL amino acid sequence:

(SEQ ID NO: 5)

<u>EIVLTQSPATLSLSPGERATLSCRASQSISDYLHWYQQKP</u>

<u>GQAPRLLIYYASQSITGIPARFSGSGSGTDFTLTISSLEP</u>

<u>EDFAVYYCQNGHSFPPTFGGGTKVEIK</u>

Humanized BCMA (PMC307) scFv Protein:

(SEQ ID NO: 6)

QVQLVQSGAEVKKPGSSVKVSCKASGYTFTSYVMHWVRQA

PGQGLEWMGYIIPYNDATKYAQKFQGRVTITADKSTSTAY

MELSSLRSEDTAVYYCARYNYDGYFDVWGQGTLVTVSSGG

GGSGGGGSGGGGSEIVLTQSPATLSLSPGERATLSCRASQ

SISDYLHWYQQKPGQAPRLLIYYASQSITGIPARESGSGS

GTDFTLTISSLEPEDFAVYYCQNGHSFPPTFGGGTKVEI

<u>K</u>

Example 2. Humanized BCMA-CAR Sequences

Example 2A. Humanized BCMA-CAR Sequences (with CD28 as a Co-Stimulating Domain)

The scheme of humanized (PMC307) BCMA-CAR construct is shown on FIG. 3. Lentiviral vector with EF1a promoter was used for cloning of humanized scFv CAR sequences.

The BCMA-CAR structure includes human CD8 signaling peptide, humanized BCMA scFv ($V_H$-Linker-$V_L$), CD8 hinge, CD28 transmembrane, CD28 co-stimulating domain, activation domains CD3 zeta (FIG. 3).

The nucleotide sequences and some of the amino acid sequences of CD8 signaling-BCMA scFv ($V_H$-Linker-$V_L$)-CD8 hinge-CD28 TM-CD28-CD3-zeta are shown below.

```
<CD8 leader (CD 8 signaling)>
Nucleotide
                                       (SEQ ID NO: 7)
ATGGCCTTACCAGTGACCGCCTTGCTCCTGCCGCTGGCCT

TGCTGCTCCACGCCGCCAGGCCG

Amino Acid
                                       (SEQ ID NO: 8)
MALPVTALLLPLALLLHAARP Gctagc <Nhe I site>
Amino Acid Sequence
AS <Humanized BCMA, PMC 307 scFv>
V_H-linker-V_L, see Example 1 for nucleic acid
sequences and amino acid sequences.
<XhoI restriction site>
CTCGAG Amino acid sequence
LE <CD8 hinge>
Nucleotide
                                       (SEQ ID NO: 9)
AAGCCCACCACGACGCCAGCGCCGCGACCACCAACACCGG

CGCCCACCATCGCGTCGCAGCCCCTGTCCCTGCGCCCAGA

GGCGAGCCGGCCAGCGGCGGGGGCGCAGTGCACACGAGG

GGGCTGGACTTCGCCAGTGAT

Amino Acid
                                       (SEQ ID NO: 10)
KPTTTPAPRPPTPAPTIASQPLSLRPEASRPAAGGAVHTRGL

DFASD
```

-continued

<Spacer>
Nucleotide sequence
aagccc

Amino Acid sequence
KP

<CD28 transmembrane>
Nucleotide
(SEQ ID NO: 11)
TTTTGGGTGCTGGTGGTGGTTGGTGGAGTCCTGGCTTGCT

ATAGCTTGCTAGTAACAGTGGCCTTTATTATTTTCTGGGT

G

Amino Acid
(SEQ ID NO: 12)
FWVLVVVGGVLACYSLLVTVAFIIFWV

<CD28 co-stimulatory>
Nucleotide
(SEQ ID NO: 13)
AGGAGTAAGAGGAGCAGGCTCCTGCACAGTGACTACATGA

ACATGACTCCCCGCCGCCCCGGGCCCACCCGCAAGCATTA

CCAGCCCTATGCCCCACCACGCGACTTCGCAGCCTATCGC

TCC

Amino acid
(SEQ ID NO: 14)
RSKRSRLLHSDYMNMTPRRPGPTRKHYQPYAPPRDFAAYR

S

<CD3 zeta> with stop codons (TAAtag)
bolded at end
Nucleotide
(SEQ ID NO: 15)
AGAGTGAAGTTCAGCAGGAGCGCAGACGCCCCCGCGTACC

AGCAGGGCCAGAACCAGCTCTATAACGAGCTCAATCTAGG

ACGAAGAGAGGAGTACGATGTTTTGGACAAGAGACGTGGC

CGGGACCCTGAGATGGGGGGAAAGCCGCAGAGAAGGAAGA

ACCCTCAGGAAGGCCTGTACAATGAACTGCAGAAAGATAA

GATGGCGGAGGCCTACAGTGAGATTGGGATGAAAGGCGAG

CGCCGGAGGGGCAAGGGGCACGATGGCCTTTACCAGGGTC

TCAGTACAGCCACCAAGGACACCTACGACGCCCTTCACAT

GCAGGCCCTGCCCCCTCGCTAAtag

Amino acid
(SEQ ID NO: 16)
RVKFSRSADAPAYQQGQNQLYNELNLGRREEYDVLDKRRG

RDPEMGGKPQRRKNPQEGLYNELQKDKMAEAYSEIGMKGE

RRRGKGHDGLYQGLSTATKDTYDALHMQALPPR

<EcoRI restriction site>
gaattc

Translated amino-acid sequence of
humanized BCMA-CAR protein (PMC307)
(SEQ ID NO: 17)
MALPVTALLLPLALLLHAARPASQVQLVQSGAEVKKPGSS

VKVSCKASGYTFTSYVMHWVRQAPGQGLEWMGYIIPYNDA

TKYAQKFQGRVTITADKSTSTAYMELSSLRSEDTAVYYCA

RYNYDGYFDVWGQGTLVTVSSGGGGSGGGGSGGGGSEIVL

TQSPATLSLSPGERATLSCRASQSISDYLHWYQQKPGQAP

RLLIYYASQSITGIPARFSGSGSGTDFTLTISSLEPEDFA

VYYCQNGHSFPPTFGGGTKVEIKLEKPTTTPAPRPPTPAP

TIASQPLSLRPEASRPAAGGAVHTRGLDFASDKPFWVLVV

VGGVLACYSLLVTVAFIIFWVRSKRSRLLHSDYMNMTPRR

PGPTRKHYQPYAPPRDFAAYRSRVKFSRSADAPAYQQGQN

QLYNELNLGRREEYDVLDKRRGRDPEMGGKPQRRKNPQEG

LYNELQKDKMAEAYSEIGMKGERRRGKGHDGLYQGLSTAT

KDTYDALHMQALPPR

Example 2B. Humanized BCMA-CAR Sequences
(with 4-1BB as a co-stimulating domain)
We also prepared CAR with 41BB domain
instead of CD28 as a costimulatory domain.
<41BB domain>
Nucleotide sequence:
(SEQ ID NO: 18)
AAACGGGGCAGAAAGAAACTCCTGTATATATTCAAACAAC

CATTTATGAGACCAGTACAAACTACTCAAGAGGAAGATGG

CTGTAGCTGCCGATTTCCAGAAGAAGAAGAAGGAGGATGT

GAACTG

Amino acid sequence
(SEQ ID NO: 19)
KRGRKKLLYIFKQPFMRPVQTTQEEDGCSCRFPEEEEGGCEL

<hBCMA ScFV-41BB-CD3 CAR> (PMC714)
(SEQ ID NO: 20)
MALPVTALLLPLALLLHAARPASQVQLVQSGAEVKKPGSS

VKVSCKASGYTFTSYVMHWVRQAPGQGLEWMGYIIPYNDA

TKYAQKFQGRVTITADKSTSTAYMELSSLRSEDTAVYYCA

RYNYDGYFDVWGQGTLVTVSSGGGGSGGGGSGGGGSEIVL

TQSPATLSLSPGERATLSCRASQSISDYLHWYQQKPGQAP

RLLIYYASQSITGIPARFSGSGSGTDFTLTISSLEPEDFA

VYYCQNGHSFPPTFGGGTKVEIKLEKPTTTPAPRPPTPAP

TIASQPLSLRPEASRPAAGGAVHTRGLDFASDKPFWVLVV

VGGVLACYSLLVTVAFIIFWVKRGRKKLLYIFKQPFMRPV

QTTQEEDGCSCRFPEEEEGGCELRVKFSRSADAPAYQQGQ

NQLYNELNLGRREEYDVLDKRRGRDPEMGGKPQRRKNPQE

GLYNELQKDKMAEAYSEIGMKGERRRGKGHDGLYQGLSTA

TKDTYDALHMQALPPR

Example 3. CAR Lentivirus Production

The inventors generated humanized BCMA-ScFv-CAR constructs and cloned them into lentiviral vectors with (a) promoter EF1 and CD28 costimulatory domain for PMC307, or (b) MNDU3 promoter and 41BB costimulatory domain for PMC714. The lentiviral CAR construct contained the humanized BCMA ScFv-CD28/4-1BB-CD3zeta insert.

Lentiviruses were generated in 293T cells by the standard procedure as described in [7] containing either ampicillin-resistance (AmpR) genes or kanamycin-resistance (KanR)

gene; the titers were established by real time PCR. Then equal dose of lentiviruses was used for transduction of T cells.

Example 4. Peripheral Blood Mononuclear Cell (PBMC) Isolation from Whole Blood

Whole blood (Stanford Hospital Blood Center, Stanford, CA) was collected from individual or mixed donors (depending on the amount of blood required) in 10 mL Heparin vacutainers (Becton Dickinson). Approximately 10 ml of whole anti-coagulated blood was mixed with sterile phosphate buffered saline (PBS) buffer for a total volume of 20 ml in a 50 ml centrifuge tube (PBS, pH 7.4, without $Ca^{+2}$ and $Mg^{+2}$). The blood/PBS (20 ml) was layered on top of 15 mL of Ficoll-Paque PLUS (GE Healthcare) in a conical centrifuge tube gently, and the sample was centrifuged at 400×g for 30-40 min at room temperature. The layer of cells containing peripheral blood mononuclear cells (PBMC) at the diluted plasma/Ficoll interface was removed, washed, and centrifuged at 200×g for 10 min at room temperature. Cells were counted with a hemocytometer. The PBMC were washed once with CAR-T media (AIM V® (serum-free medium) ALBUMAX® (bovine serum albumin medium) (Life Technologies), with 5% AB serum and 1.25 µg/mL amphotericin B (Gemini Bioproducts, Woodland, CA), 100 U/mL penicillin, and 100 µg/mL streptomycin) and used for experiments or were frozen at −80° C.

Example 5. T-Cell Activation from PBMC

The isolated PBMC cells are resuspended in CAR-T medium with 300U/mL huIL2 (from a 1000× stock; Invitrogen) and mixed with CD3-CD28 beads at a 1:1 bead-to-cell ratio. The cells are incubated at 37° C. in the presence of CO2 for 24 hours before viral transduction.

Example 6. T-Cell Transduction and Expansion

Following activation of PBMC, cells were incubated for 24 hours at 37° C., 5% $CO_2$. To each well of $1\times10^6$ cells, $5\times10^6$ lentivirus and 2 µL/mL of media of Transplus (Alstem, Richmond, CA) (a final dilution of 1:500) were added. Cells were incubated for an additional 24 hours before repeating the addition of virus. Cells were then grown in the continued presence of 300 U/ML of IL-2 fresh medium with IL-2 for a period of 12-14 days (total incubation time was dependent on the final umber of CAR-T cells required). Cells concentrations were analyzed every 2-3 days, with media being added at that time to dilute the cell suspension to $1\times10^6$ cells/mL.

Example 7. Humanized BCMA-CAR-T Cells Expressed BCMA scFv

We designed humanized BCMA-CAR-T cells with humanized BCMA-CAR construct shown in Example 2. We used Mock scFv with unrelated ScFv and generated Mock-CAR-T cells as a negative control. Humanized BCMA-CAR-positive cells were detected after transduction of lentiviral humanized BCMA CAR into T cells.

Figure 4A:
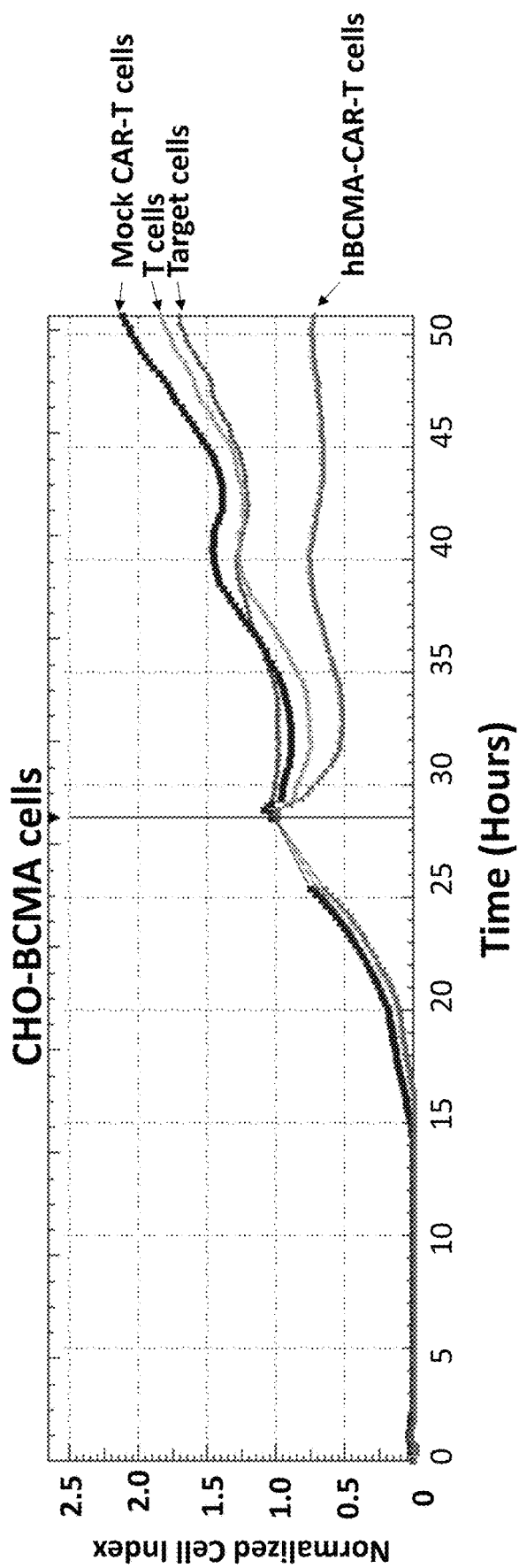
FIGS. 4A-4B show humanized BCMA-CAR-T cells kill CHO-BCMA cells but not CHO cells. XCELLIGENCE® (real-time cell analyzer) real-time cytotoxicity assay was used for detection of humanized BCMA-CAR-T cell cytotoxicity. Normalized cell index is shown on Y-axis, and time is shown on X-axis.
Figure 4B:
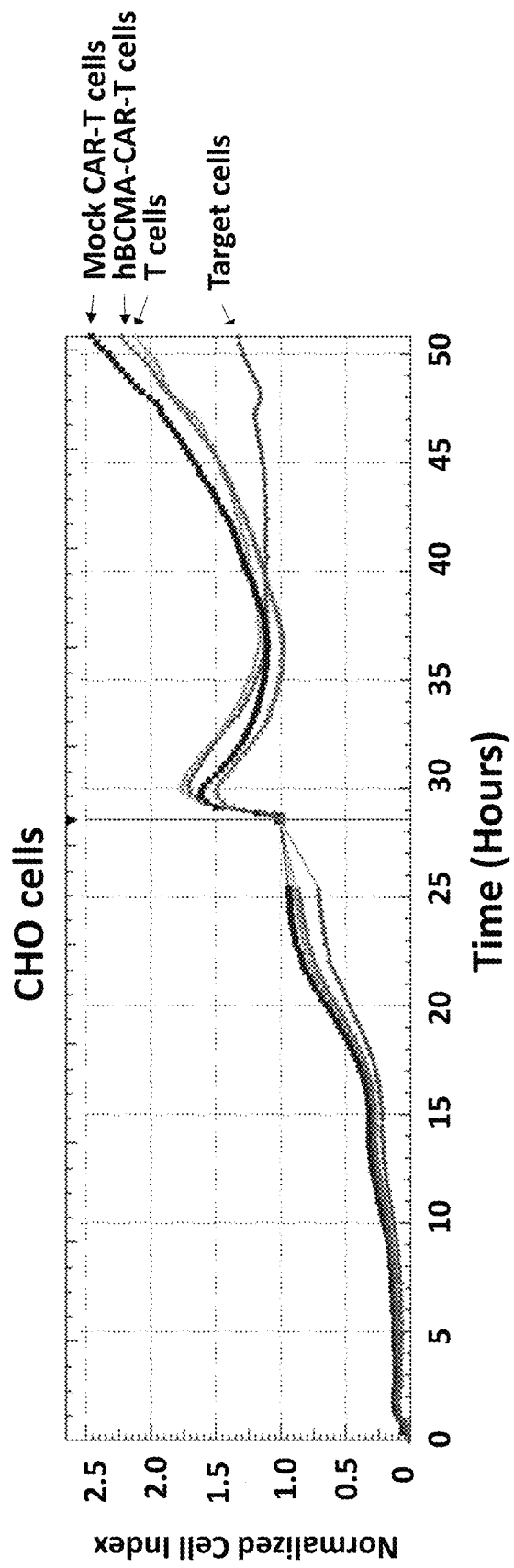

Humanized BCMA-CAR construct was detected by FACS analysis with fluorescently labeled recombinant BCMA protein. Humanized BCMA-CAR-T-positive cells after transduction of lentiviral humanized BCMA-CAR into T cells were also detected by FACS analysis with fluorescently labeled recombinant BCMA protein Example 8. Humanized BCMA-CAR-T Cells Killed CHO-BCMA Cells but not CHO Cells We incubated humanized BCMA-CAR-T cells with target CHO-BCMA target cells and CHO (BCMA-negative) control cells. Humanized BCMA-CAR-T cells specifically killed CHO-BCMA cells (FIG. 4A) but not CHO cells (FIG. 4B). The results demonstrate high specificity of humanized BCMA-CAR-T cells to target BCMA antigen and to kill BCMA-positive cells.

Figure 5:
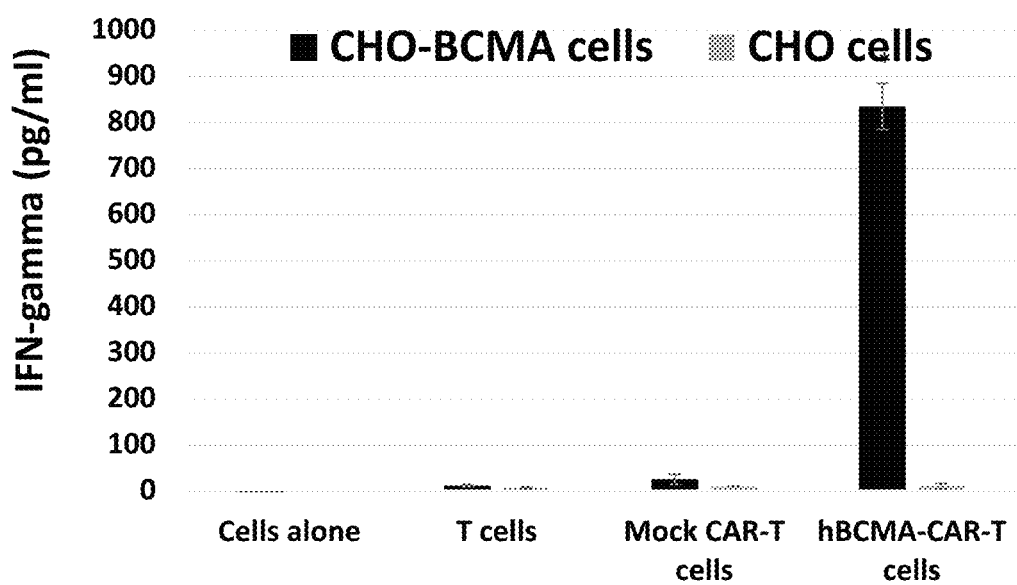
FIG. 5 shows that humanized BCMA-CAR-T cells secreted high level of IFN-gamma with CHO-BCMA-positive cells, but not with BCMA-negative CHO control cells. $p<0.05$ IFN-gamma secretion in CHO-BCMA cells of BCMA-CAR-T cells versus T cells and Mock CAR-T cells.

Example 9. Humanized CAR-T Cells Secreted IFN-Gamma Against Target CHO-BCMA Cells Significantly but not Against CHO Cells We collected supernatant after co-incubation of humanized BCMA-CAR-T cells with target CHO-BCMA or control CHO cells and performed IFN-gamma assay. BCMA-CAR-T cells secreted IFN-gamma with CHO-BCMA cells but not with negative control CHO cells (FIG. 5). Similar results were also obtained with CAR-T cells generated with lentiviral hBCMA (PMC307 scFV)-CAR with 41BB domain, and MNDU3 promoter (data not shown). The results confirm the specificity of humanized BCMA-CAR-T cells.

Figure 6:
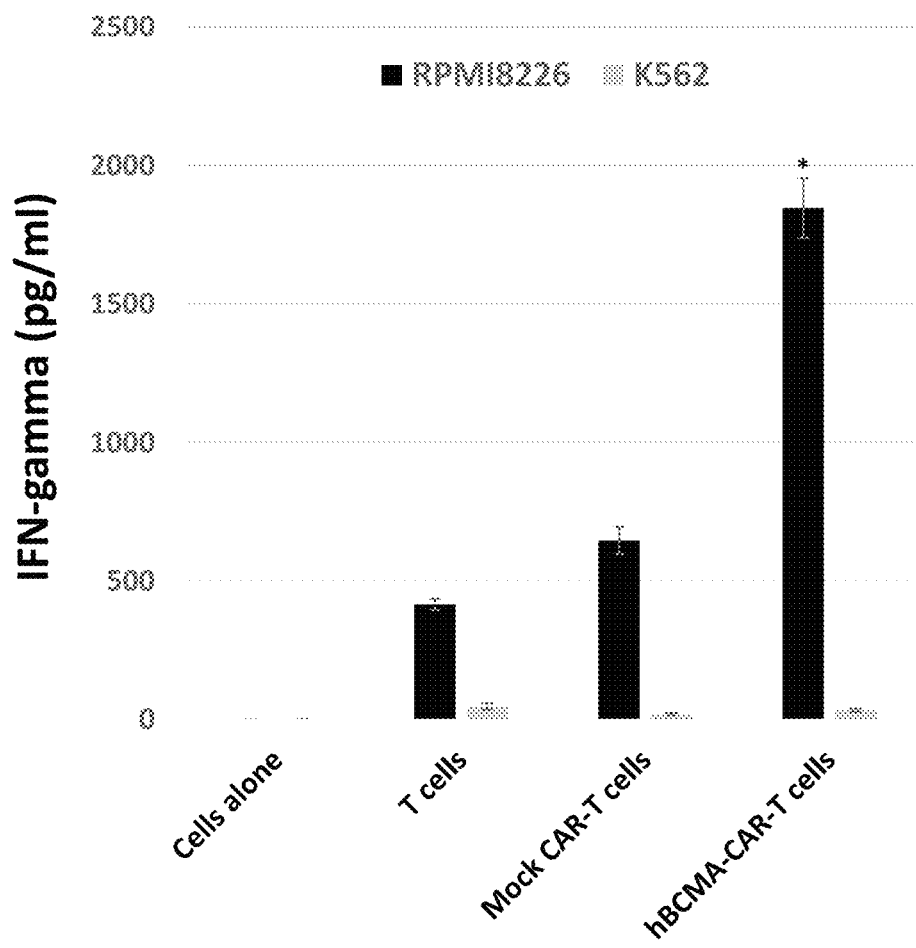
FIG. 6 shows humanized BCMA-CAR-T cells secreted high level of IFN-gamma against multiple myeloma cells but not against BCMA-negative K562 control cells. *$p<0.05$, IFN-gamma secretion in multiple myeloma cells of BCMA-CAR-T cells versus T cells and Mock-CAR-T cells.

Example 10. Humanized CAR-T Cells Secreted High Levels of IFN-Gamma Against BCMA-Positive RPMI8226 Multiple Myeloma Cells but not Against BCMA-Negative K562 Leukemia Cells We incubated BCMA-CAR-T cells with multiple myeloma cancer cells RPMI8266, and BCMA-negative K562 cells (chronic myelogenous leukemia cells) and performed ELISA with IFN-gamma using kit from Fisher, according to manufacturer's protocol. Humanized BCMA-CAR-T cells secreted high level of IFN-gamma against BCMA-positive multiple myeloma cancer cells but not against BCMA-negative K562 cells (FIG. 6). The level of killing and secretion of IFN-gamma was significantly higher with BCMA-CAR-T cells than with T cells and Mock CAR-T cells. This confirms specificity of humanized BCMA-CAR-T cells against hematological BCMA-positive cells.

Example 11. Humanized BCMA-41BB-CD3 (PMC714) Killed BCMA-Positive Target Cells

Figure 7A:
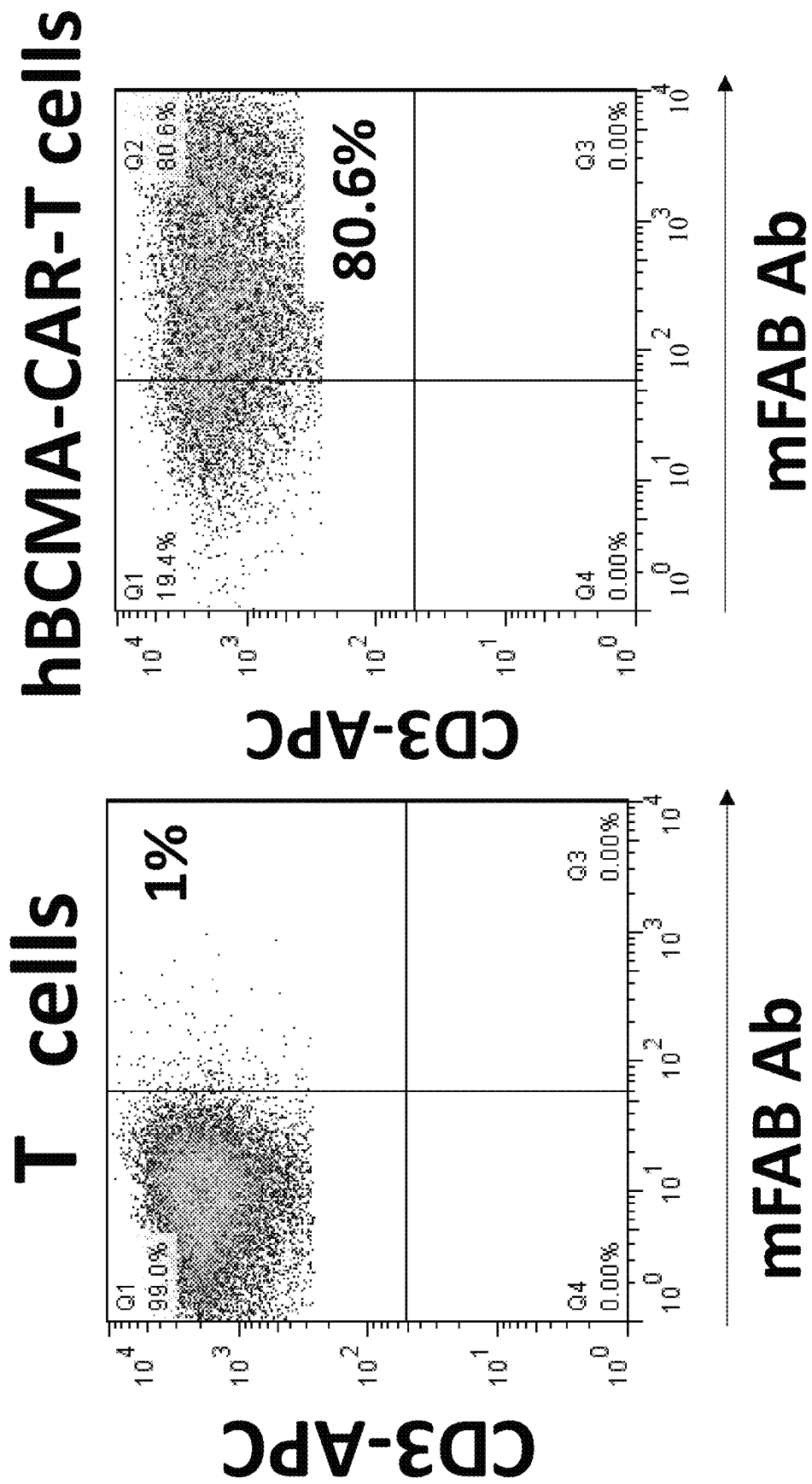
FIGS. 7A-7B show high expression by FACS of CAR+ cells after transduction with hBCMA-41BB-CD3-CAR lentivirus T cells. FACS was performed with CD3 antibody-Y axis, and either mouse FAB antibody (X-axis, 7A) or fluorescently labelled BCMA-protein (X-axis, 7B).
Figure 7B:
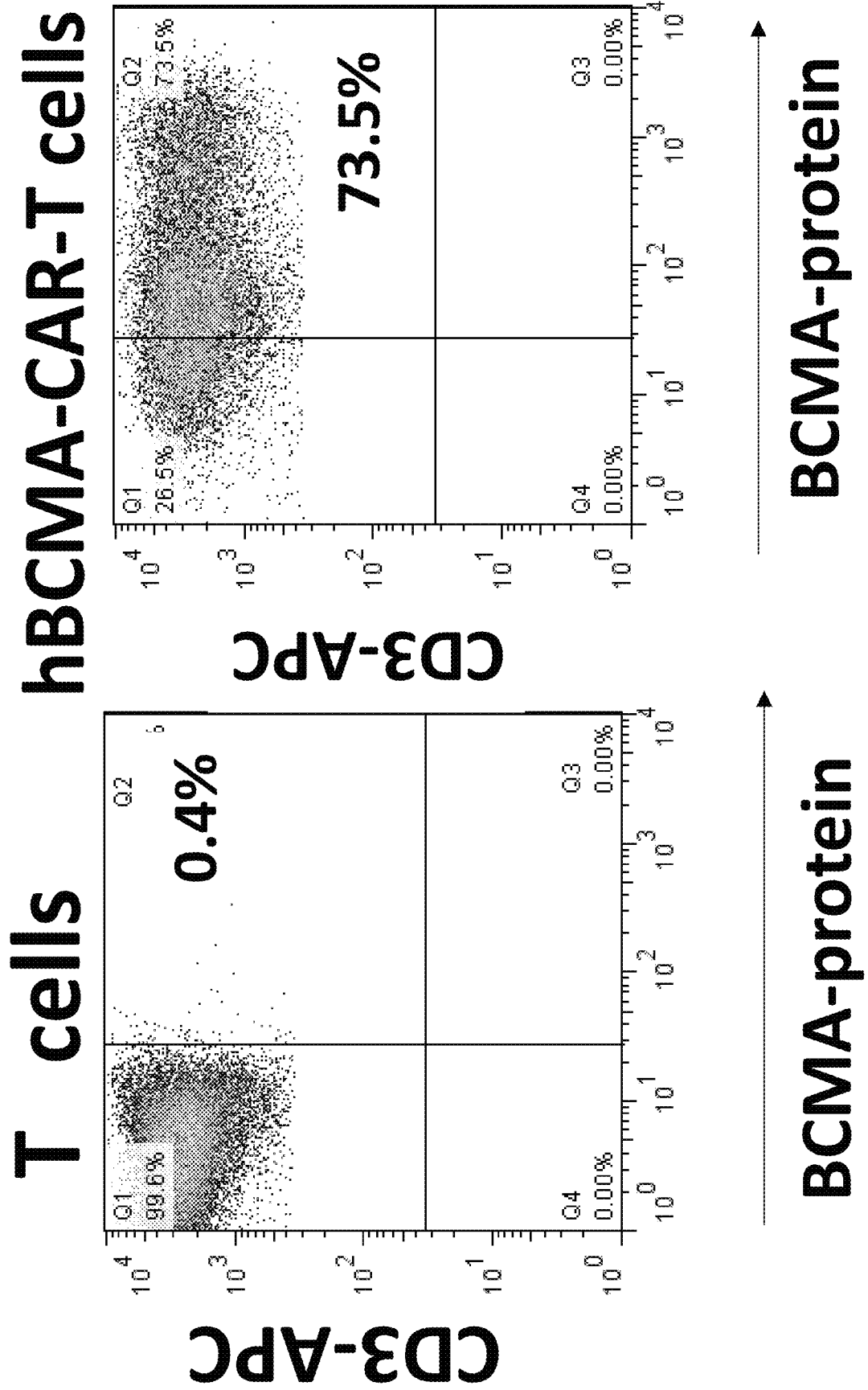

We prepared hBCMA-307scFv-CAR with 41BB-CD3 domain and MNDU3 promoter (Examples 2B and 3, PMC714). PMC714 CAR-T cells had high CAR expression that was 80.6% CAR-positive cells with anti-mouse $(Fab)_2$ antibody (FIG. 7A, right panel) and 73% with fluorescently-labeled BCMA-protein (FIG. 7B, right panel). The control T cells had minimal staining with both (0.4-1%) (FIGS. 7A-7B, left panels).

Figure 8A:
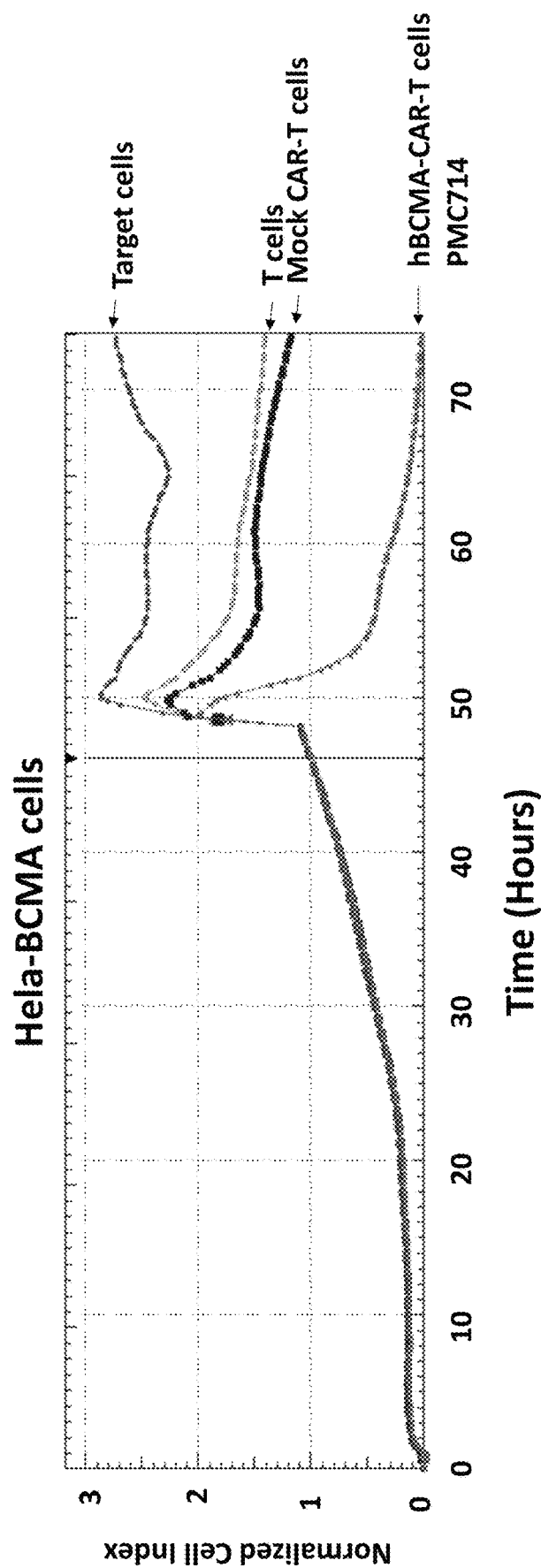
FIGS. 8A-8B show killing of BCMA-positive Hela-BCMA target cells (8A) and control BCMA-negative Hela-CS1 cells (8B) by hBCMA-41BB-CD3-CAR-T cells.
Figure 8B:
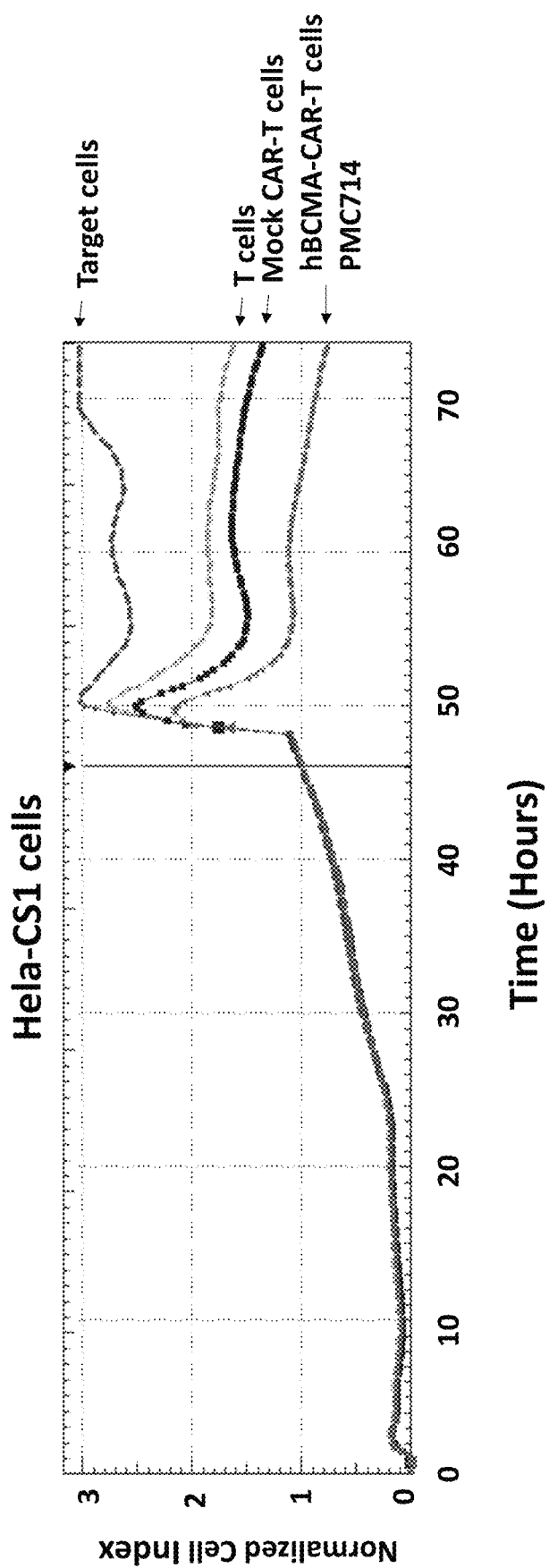

FIG. 8 shows hBCMA-41BB-CD3-CAR-T cells killed more BCMA-positive Hela-BCMA target cells (FIG. 8A) than BCMA-negative Hela-CS1 cells (FIG. 8B)

Figure 9:
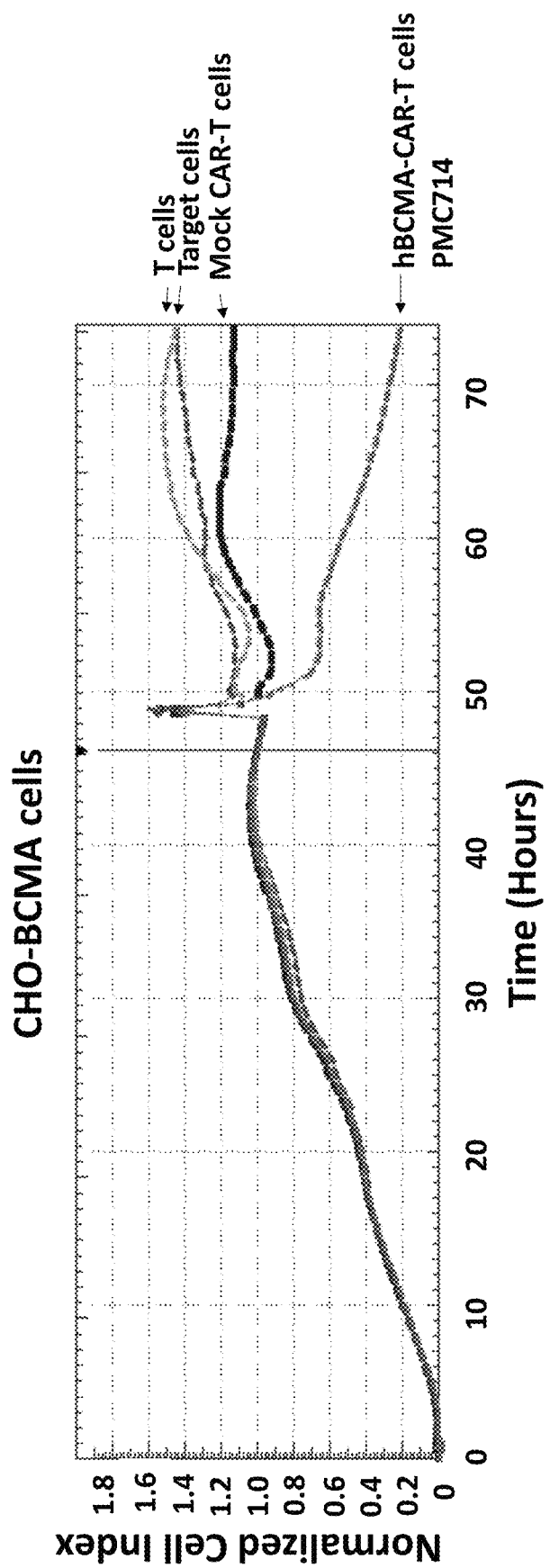
FIG. 9 shows humanized BCMA-41BB-CD3-CAR-T cells (PMC714) killed CHO-BCMA target cells.

FIG. 9 shows high killing by hBCMA-41BB-CD3-CAR-T cells with CHO-BCMA-target cells.

Figure 10:
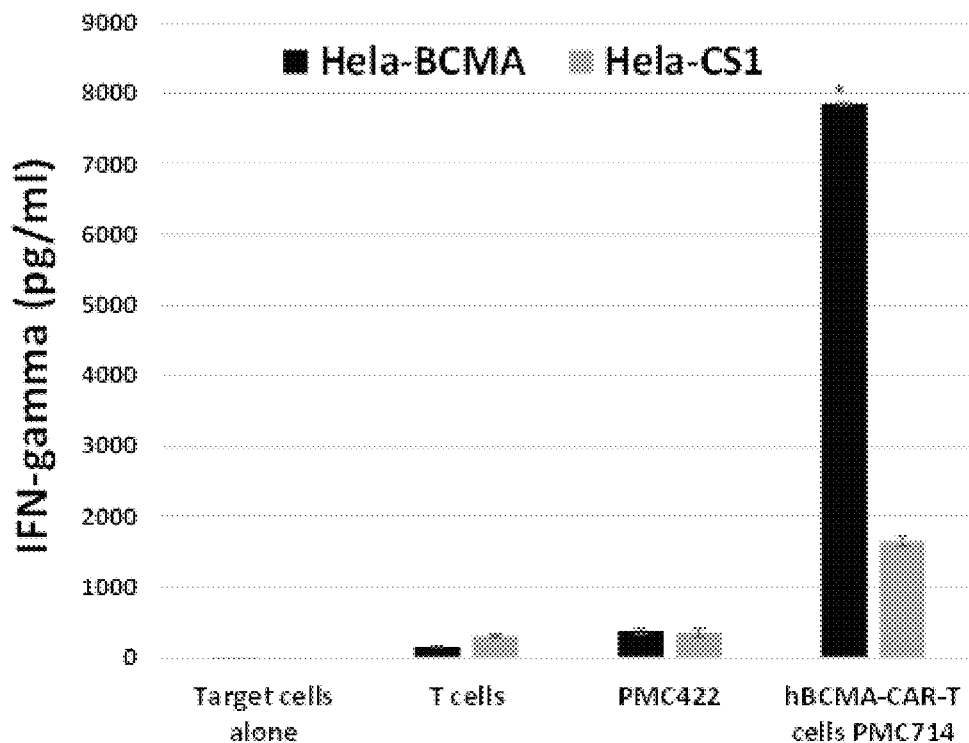
FIG. 10 shows that humanized BCMA-CAR-T cells (PMC714) secreted significantly higher levels of IFN-gamma with Hela-BCMA target cells than with Hela-CS1 target cells ($p<0.05$, Student's t-test).

Example 12. Humanized BCMA-41BB-CD3 (PMA714) Secreted High Level of IFN-Gamma with BCMA-Positive Cells but not with BCMA-Negative Target Cells Humanized BCMA-41BB-CD3-CAR-T cells (PMC714) secreted significantly higher level of IFN-gamma with BCMA-positive Hela-BCMA target cells than with BCMA-negative Hela-CS1 target cells (FIG. 10). These CAR-T cells secreted high level of IFN-gamma with CHO-BCMA target cells (FIG. 11).

FIG. 10 shows that humanized BCMA-CAR-T cells (PMC714) secreted significantly higher levels of IFN-gamma with Hela-BCMA target cells than with Hela-CS1 target cells (p<0.05, Student's t-test).

Figure 11:
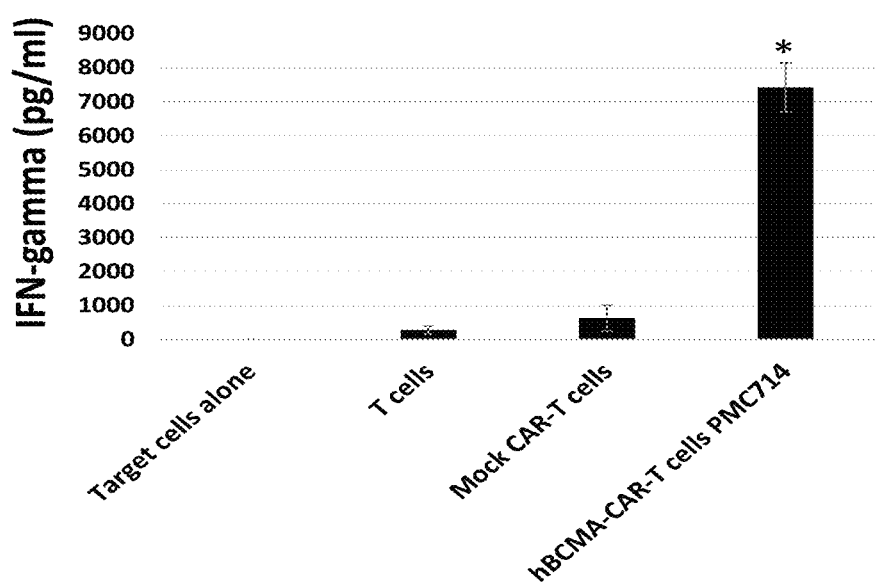
FIG. 11 shows that humanized BCMA-CAR-T cells (PMC714) secreted significantly higher level of IFN-gamma than T and Mock-CAR-T cells using BCMA-positive CHO-BCMA target cells (bottom panel). $P<0.05$, Student's t-test.

FIG. 11 shows that humanized BCMA-CAR-T cells (PMC714) secreted significantly higher level of IFN-gamma than T and Mock-CAR-T cells using BCMA-positive CHO-BCMA target cells (bottom panel). P<0.05, Student's t-test.

Figure 12:
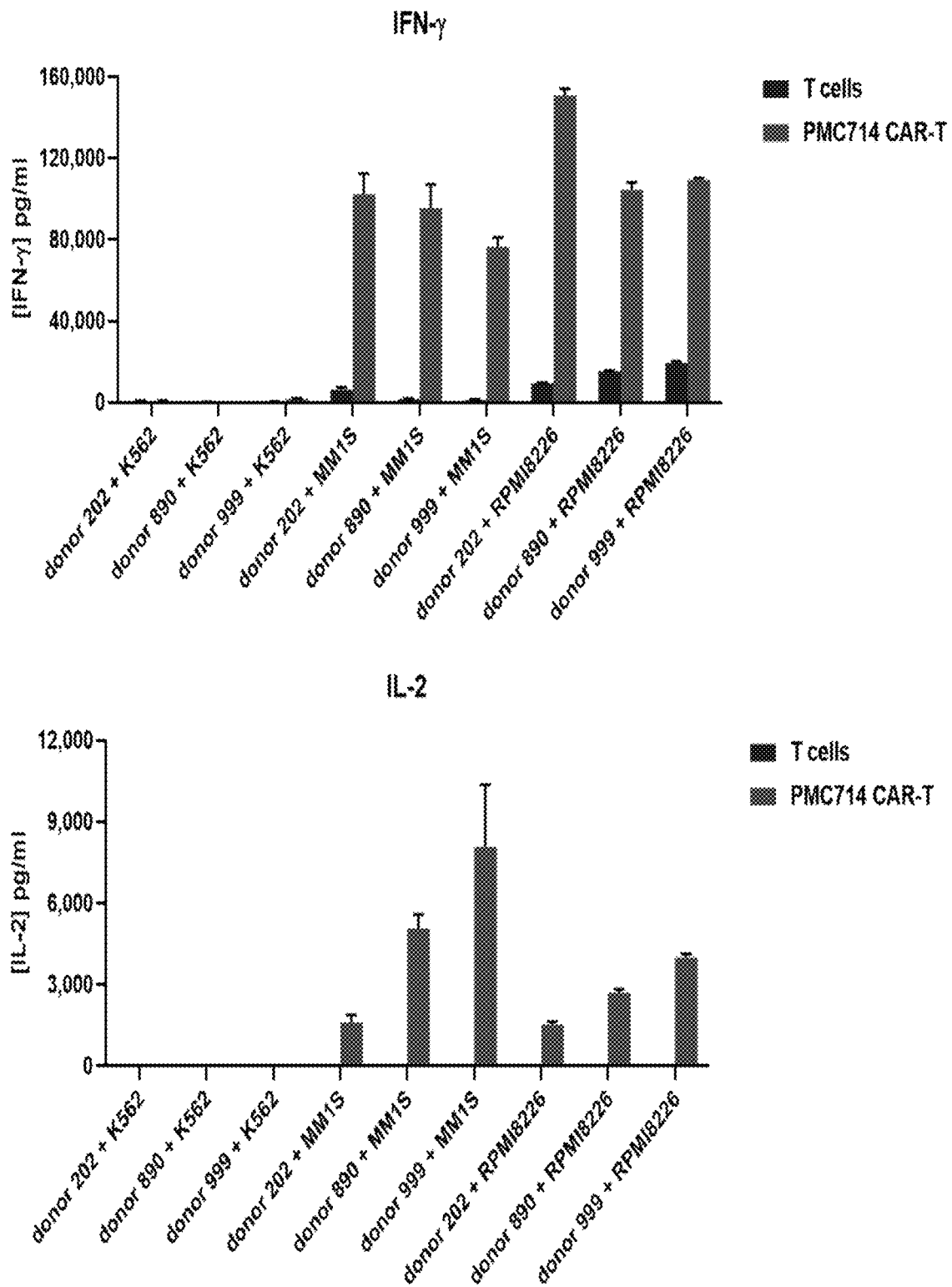
FIG. 12 shows cytokine production in response to myeloma cells. PMC714 anti-BCMA CAR-T cells or control T cells were cultured overnight with multiple myeloma cells endogenously expressing BCMA (MM1S, RPMI8226) or control cells lacking BCMA (K562). Medium was collected from the cultures, centrifuged to remove cells and analyzed by ELISA for the levels of IFN-γ and IL-2 The average of two replicates is shown. For all 3 donors cultured with MM1S cells or RPMI8226 cells, the p values for CAR-T cells (shown on the left) vs T cells (shown on the right) are <0.0001 for IFN-γ. For IL-2, the p values for CAR-T cells vs T cells are <0.0001 for donors 890 and 999, 0.0002 for donor 202+MM1S, and 0.0003 for donor 202+ RPMI8226 (2-way ANOVA with Sidak's post-hoc test). Left bar show T cells and right bar show CAR-T cells for each donor.

Example 13. Humanized BCMA-CAR-T Cells (PMC714) Secreted IFN-Gamma with Multiple Myeloma Cells To determine whether PMC714 CAR-T cells respond to tumor cells endogenously expressing BCMA, the CAR-T cells or control T cells from 3 different donors (Donor 202, 890 and 999) were cultured overnight with MM1S or RPMI8226 multiple myeloma cells at a 1:1 ratio. As a negative control, the BCMA-CAR-T cells were cultured with BCMA-negative K562 non-myeloma cells. The levels of IFN-g, IL-2 and IL-6 in the cultures were then measured by ELISA. PMC714 CAR-T cells produced high levels of IFN-g and IL-2 in response to MM1S cells and RPMI8226 cells but not in response to K562 cells (FIG. 12). Control T cells produced significantly lower levels of IFN-g and IL-2. Neither CAR-T cells nor T cells produced IL-6 in response to any of the target cells.

FIG. 12. Cytokine production in response to myeloma cells. PMC714 anti-BCMA CAR-T cells or control T cells were cultured overnight with multiple myeloma cells endogenously expressing BCMA (MM1S, RPMI8226) or control cells lacking BCMA (K562). Medium was collected from the cultures, centrifuged to remove cells and analyzed by ELISA for the levels of IFN-γ and IL-2 The average of 2 replicates is shown. For all 3 donors cultured with MM1S cells or RPMI8226 cells, the p values for CAR-T cells (shown on the left) vs T cells (shown on the right) are <0.0001 for IFN-γ. For IL-2, the p values for CAR-T cells vs T cells are <0.0001 for donors 890 and 999, 0.0002 for donor 202+MM1S, and 0.0003 for donor 202+RPMI8226 (2-way ANOVA with Sidak's post-hoc test). Left bar show T cells and right bar show CAR-T cells for each donor.

Example 14. Activity of PMC714 in KanR Vector (PMC751)

In clinic, vectors with ampicillin-resistance (AmpR) genes are not recommended. Therefore, we changed AmpR in the PMC714 vector to a kanamycin-resistance (KanR) gene and called this vector PMC751. The CAR sequence itself identical to the PMC714 CAR.

CAR Expression

Figure 13:
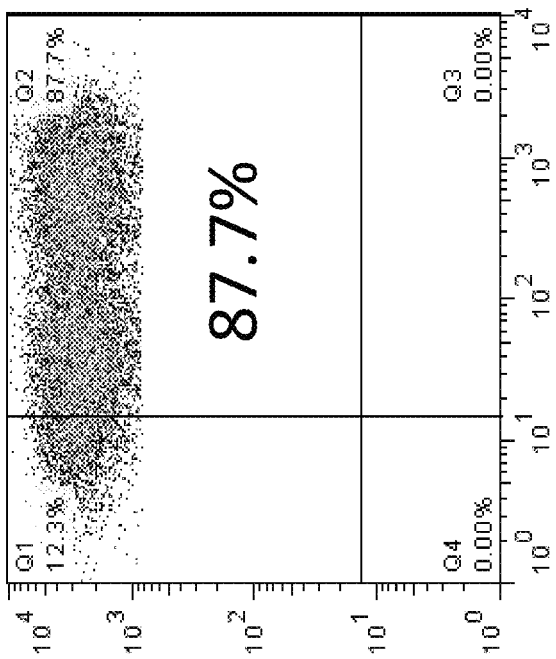
FIG. 13 is a flow cytometric analysis of PMC751-transduced T cells. Non-transduced T cells and PMC714-transduced cells were stained sequentially with biotinylated BCMA protein and PE-conjugated streptavidin (X-axis). 7-AAD was included in the stain to gate out dead cells before analysis.
Figure 13:
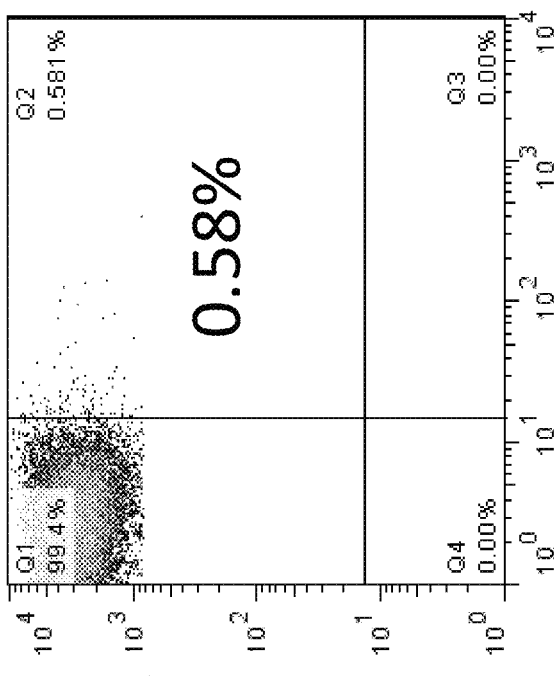

We generated PMC751 CAR-T cells and analyzed the cells by flow cytometry for the frequency of binding of these CAR-T cells. Over 87% of the PMC751 CAR-T cells bound to the biotinylated BCMA protein, indicating that these cells were BCMA-positive CAR-T cells (FIG. 13).

Cytotoxicity Assay

Figure 14A:
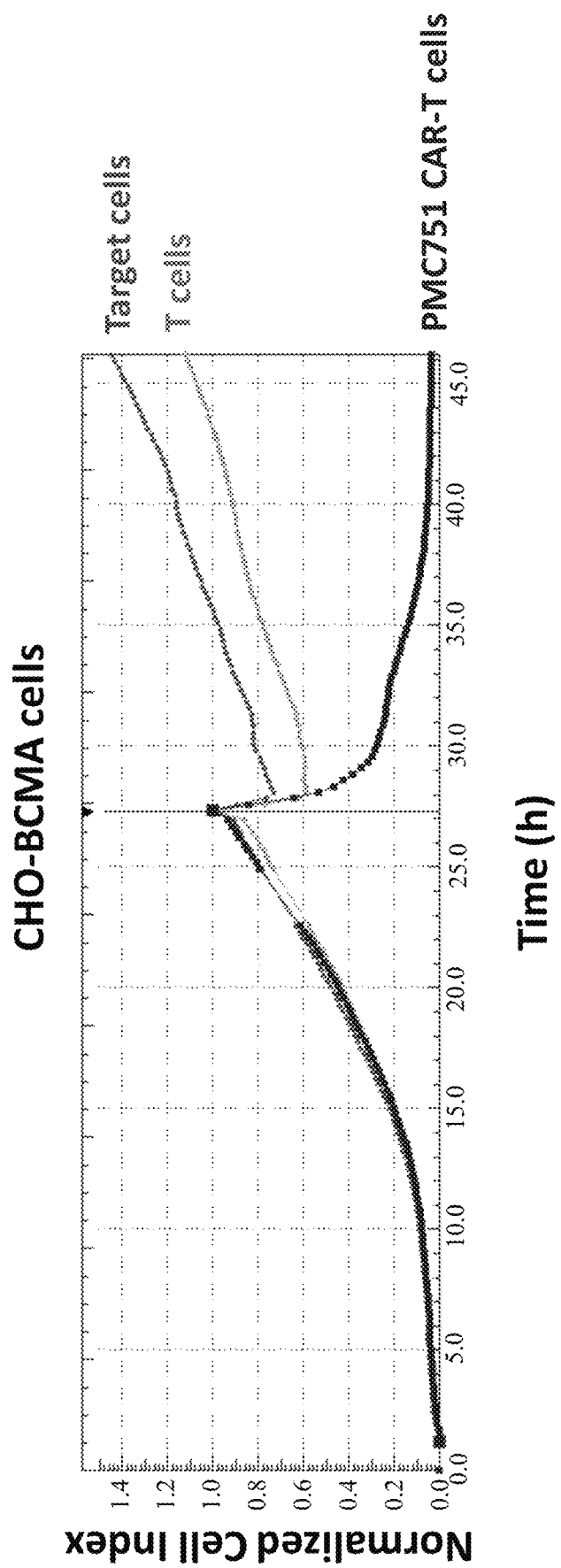
FIGS. 14A-14B show real-time cytotoxicity assay with PMC751 CAR-T cells. CHO-BCMA target cells (14A) and CHO-CS1 cells (14B) were monitored in culture as they formed monolayers. Approximately 27 hours later (vertical bar), PMC751 anti-BCMA CAR-T cells or control T cells were added at an E:T ratio of 10:1. The X-axis is time in hours and the Y-axis is the impedance of the target cell monolayer, normalized to 1.0 at the time of effector cell addition. Each trace shows the average of 3 wells. "Target cells" indicates wells that did not receive effector cells.
Figure 14B:
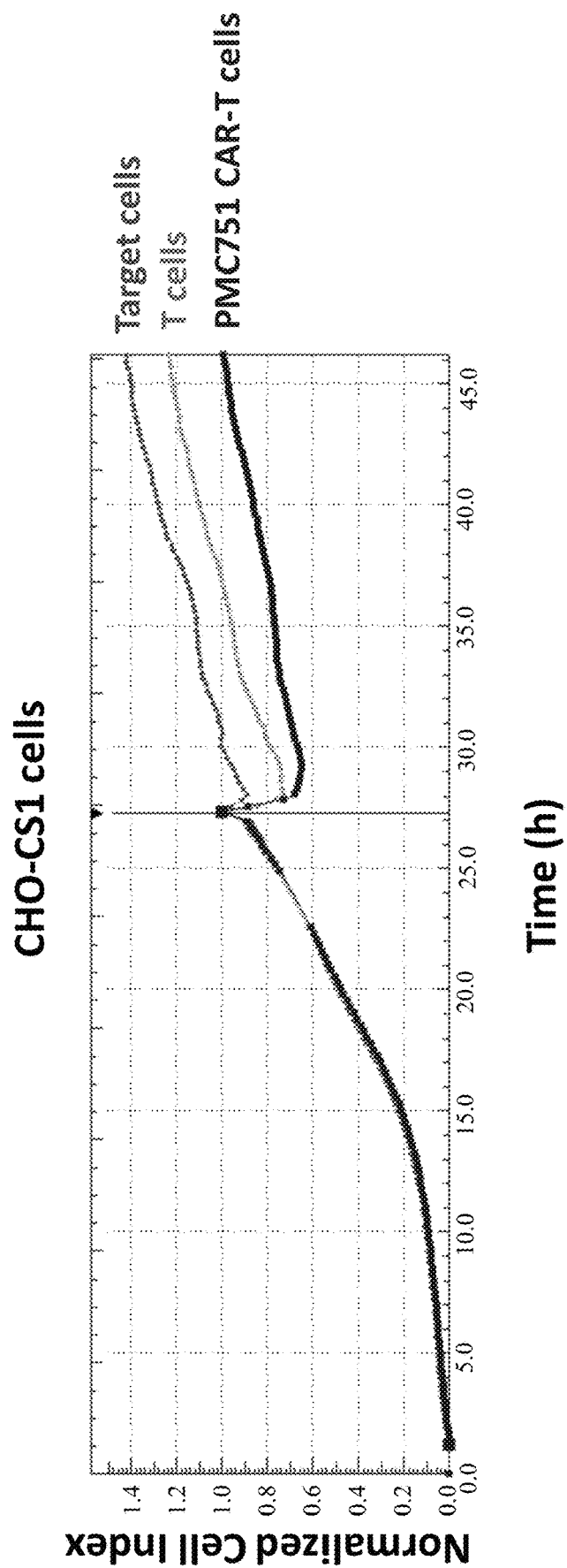

PMC751 CAR-T cells were analyzed in the RTCA assay with CHO cells expressing BCMA. At a 10:1 E:T ratio, PMC751 CAR-T cells but not control T cells were strongly cytotoxic for the target cells (FIG. 14A). In contrast, PMC751 CAR-T cells were not strongly cytotoxic for negative control target cells of CHO cells expressing CS1 (FIG. 14B). PMC751 CAR-T cells were also tested strongly cytotoxic for Hela-BCMA target cells (data not shown).

IFN-γ Production

Figure 15:
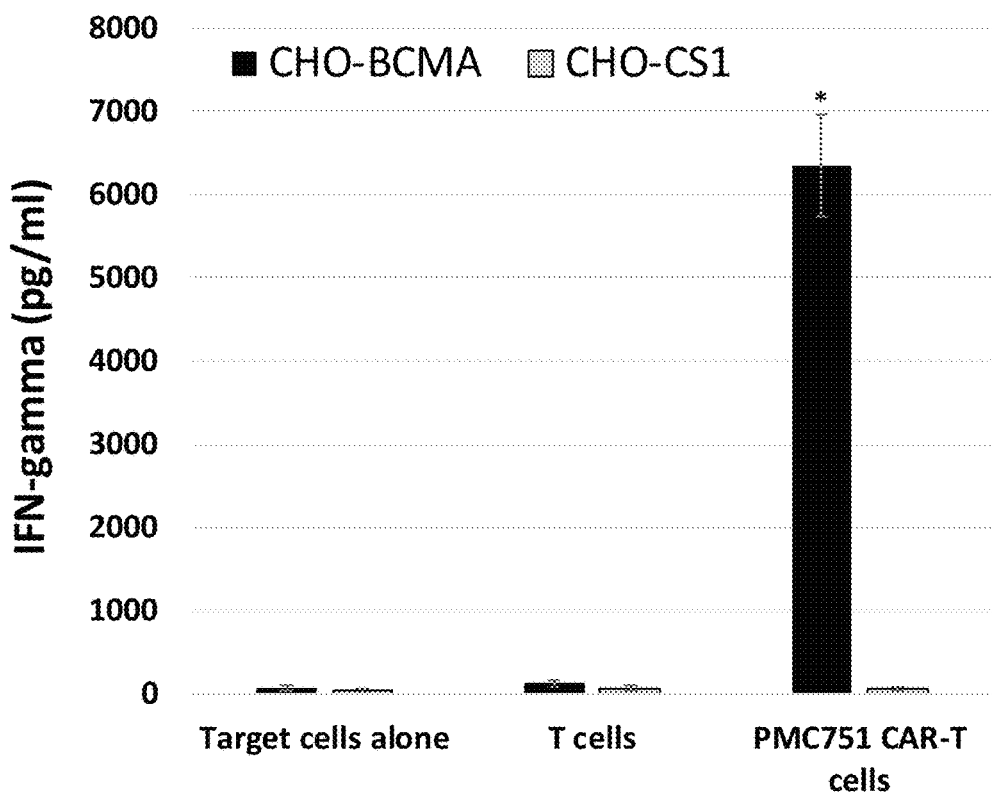
FIG. 15 shows the production of IFN-gamma by PMC751 CAR-T cells. Medium was collected from the RTCA wells, centrifuged to remove cells and analyzed by ELISA for the levels of IFN-g. PMC751 CAR-T cells exhibited IFN-γ with a p value<0.05 for CHO-BCMA vs CHO-CS1 target cells, determined by Student's t test.

Medium from the RTCA assay was analyzed by ELISA for the levels of IFN-γ. PMC751 CAR-T cells secreted significantly higher level of IFN-γ than control T cells in response to CHO-BCMA target cells but not in response to negative control CHO-CS1 target cells (FIG. 15).

Example 15. Characterization of PMC714 CAR-T Cells in a Tumor Model

Figure 16:
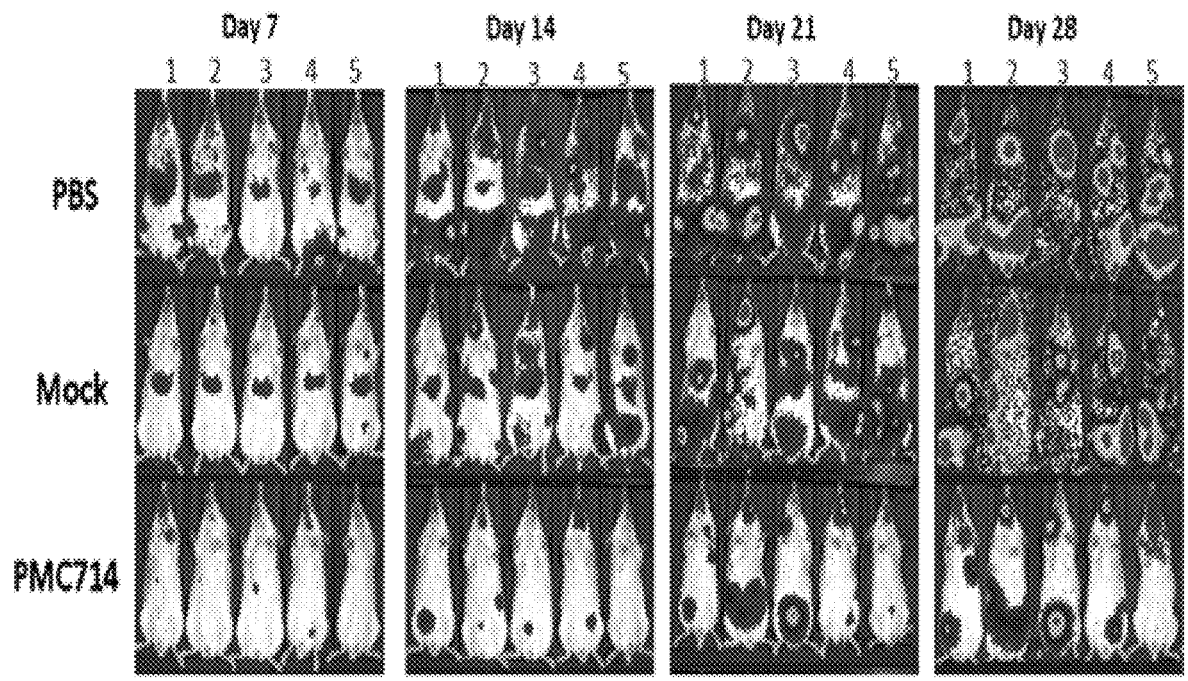
FIG. 16 shows bioluminescent imaging of labeled RPMI8226 myeloma cells in mice. Mice were treated with PBS, mock CAR-T cells or PMC714 anti-BCMA CAR-T cells.
Figure 17:
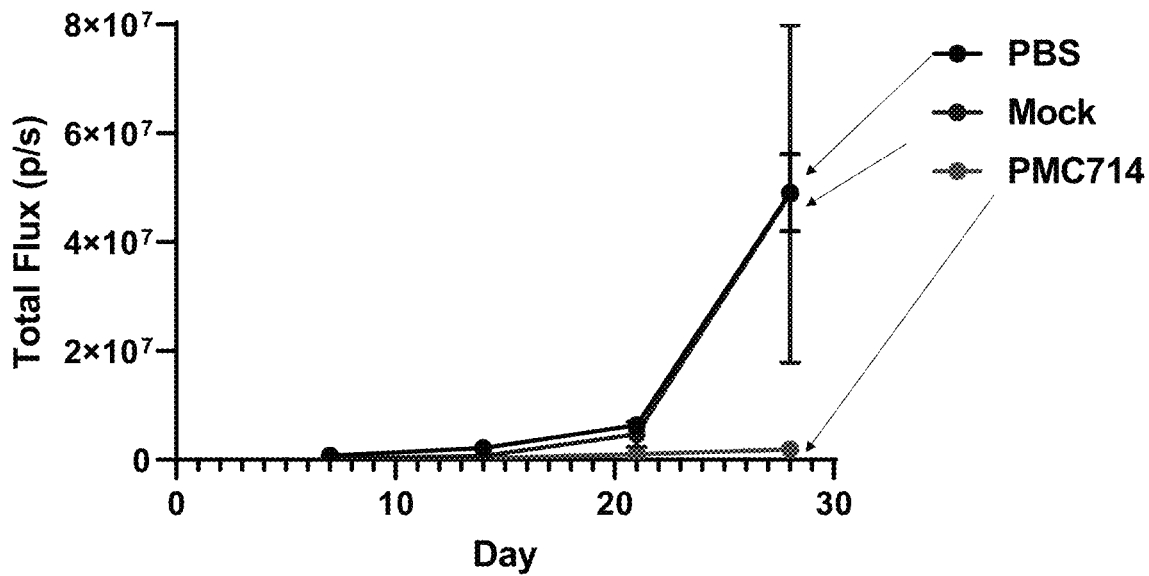
FIG. 17 shows quantitation of tumor burden in mice inoculated with RPMI8226 myeloma cells. Mice were treated with PBS (top), mock CAR-T cells (middle), or PMC714 CAR-T cells (bottom). The p value for PMC714 CAR-T cells vs Mock CAR-T cells is <0.0001 by 2-way ANOVA with Tukey's post-hoc test.

To test the PMC714 CAR-T cells for their ability to block myeloma growth in vivo, NSG immunodeficient mice were inoculated with luciferase-expressing RPMI8226 cells and then injected intravenously with CAR-T cells, mock CAR-T cells (control T cells expressing a CAR lacking the BCMA scFv), or PBS. Mice were then imaged for luminescence every week for 4 weeks. PMC714 CAR-T cells, but not control T cells, blocked the growth of the tumor cells (FIGS. 16-17).

Figure 18:
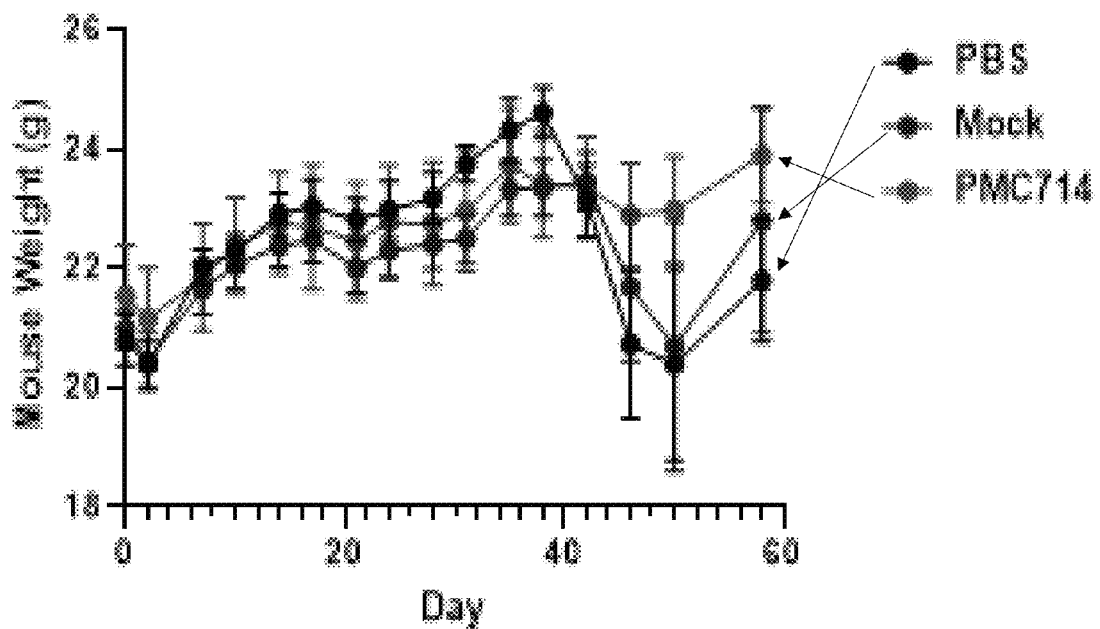
FIG. 18 shows mouse weight during the study. Average weight of each group of mice are shown.

Mice were weighed over a span of two months. The PMC714-treated mice did not lose weight during the study, indicating that the CAR-T cells were not toxic to the mice (FIG. 18).

Figure 19:
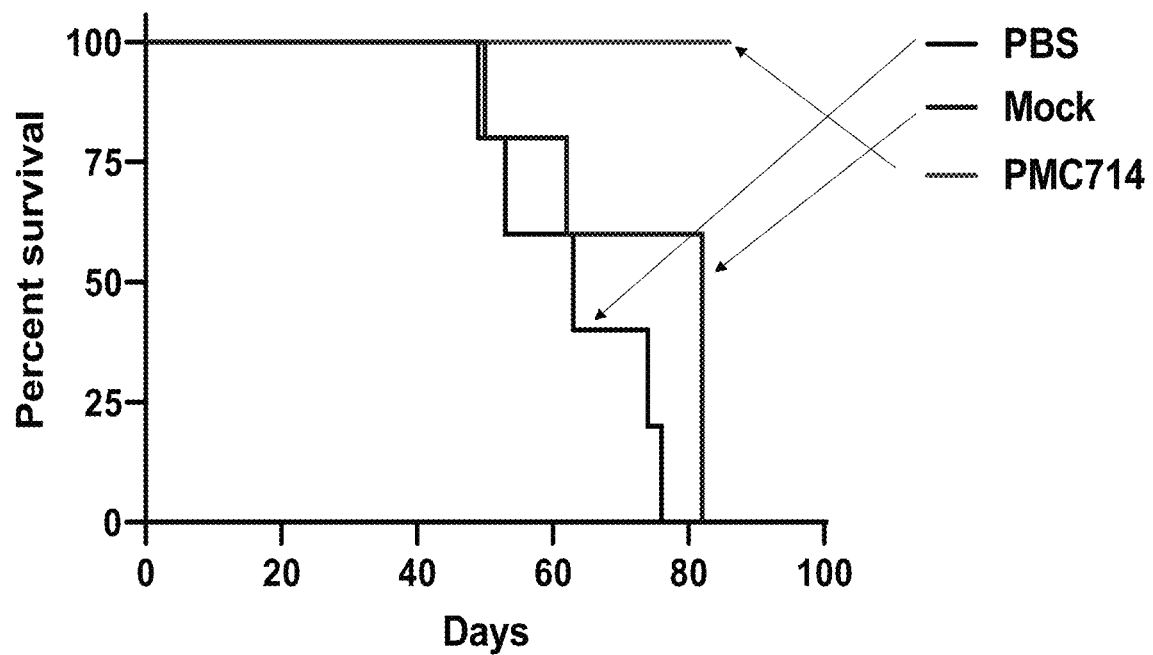
FIG. 19 shows Kaplan-Meier plot of mouse survival. p=0.0034 for PMC714 CAR-T cells vs Mock CAR-T cells by log-rank test.

The mice were analyzed for morbidity/mortality over a total of 3 months. All of the mice receiving PMC714 CAR-T cells were alive at the end of this period, whereas none of the PBS-treated mice or mock CAR-T cell-treated mice were alive (FIG. 19).

REFERENCES

1. Maus, M. V., Haas, A. R., Beatty, G. L., Albelda, S. M., Levine, B. L., Liu, X., Zhao, Y., Kalos, M., and June, C. H. (2013). T cells expressing chimeric antigen receptors can cause anaphylaxis in humans. Cancer Immunol Res 1, 26-31.
2. Maus, M. V., Grupp, S. A., Porter, D. L., and June, C. H. (2014). Antibody-modified T cells: CARs take the front seat for hematologic malignancies. Blood 123, 2625-2635.
3. Golubovskaya V, Wu L. (2016) Different Subsets of T Cells, Memory, Effector Functions, and CAR-T Immunotherapy. *Cancers,* 15, 8 (3). PMID: 26999211
4. Ali, S. A., Shi, V., Maric, I., Wang, M., Stroncek, D. F., Rose, J. J., Brudno, J. N., Stetler-Stevenson, M., Feldman, S. A., Hansen, B. G., et al. (2016). T cells expressing an anti-B-cell maturation antigen chimeric antigen receptor cause remissions of multiple myeloma. Blood 128, 1688-1700.
5. Tai, Y. T., and Anderson, K. C. (2015). Targeting B-cell maturation antigen in multiple myeloma. Immunotherapy. 7 (11): 1187-99. doi: 10.2217/imt.15.77. Epub 2015 Sep. 15. Review. PMID: 26370838
6. WO2019/195017
7. Berahovich R, Xu S, Zhou H, Harto H, Xu Q, Garcia A, Liu F, Golubovskaya V M, Wu L. FLAG-tagged CD19- specific CAR-T cells eliminate CD19-bearing solid tumor cells in vitro and in vivo. Front Biosci (Landmark Ed). 2017 Jun. 1; 22:1644-1654

---

What is claimed is:

1. A chimeric antigen receptor (CAR) comprising from N-terminus to C-terminus:
   (i) a single-chain variable fragment (scFv) comprising $V_H$ having the amino acid sequence of SEQ ID NO: 3 and $V_L$ having the amino acid sequence of SEQ ID NO: 5,
   (ii) a transmembrane domain,
   (iii) at least one co-stimulatory domain, and
   (iv) an intracellular activating domain that transmits a signal to cause activation of a biological process in a cell;
   wherein the CAR has the amino acid sequence of SEQ ID NO: 17 or 20.

* * * * *

```
                         SEQUENCE LISTING

Sequence total quantity: 20
SEQ ID NO: 1             moltype = AA   length = 184
FEATURE                  Location/Qualifiers
source                   1..184
                         mol_type = protein
                         organism = Homo sapiens
SEQUENCE: 1
MLQMAGQCSQ NEYFDSLLHA CIPCQLRCSS NTPPLTCQRY CNASVTNSVK GTNAILWTCL    60
GLSLIISLAV FVLMFLLRKI NSEPLKDEFK NTGSGLLGMA NIDLEKSRTG DEIILPRGLE   120
YTVEECTCED CIKSKPKVDS DHCFPLPAME EGATILVTTK TNDYCKSLPA ALSATEIEKS   180
ISAR                                                                184

SEQ ID NO: 2             moltype = DNA   length = 720
FEATURE                  Location/Qualifiers
source                   1..720
                         mol_type = other DNA
                         organism = Homo sapiens
SEQUENCE: 2
caggtgcagc tggtgcagag cggcgcggaa gtgaaaaaac cgggcagcag cgtgaaagtg    60
agctgcaaag cgagcggcta tacctttacc agctatgtga tgcattgggt gcgccaggcg   120
ccgggccagg gcctggaatg gatgggctat attattccgt ataacgatgc gaccaaatat   180
gcgcagaaat tcagggccg cgtgaccatt accgcggata aaagcaccag caccgcgtat   240
atggaactga gcagcctgcg cagcgaagat accgcggtgt attattgcgc gcgctataac   300
tatgatggct attttgatgt gtgggccag gcaccctgg tgaccgtgag cagcggcggc   360
ggcggcagcg gcggcggcg cagcggcggc ggcggcagcg aaattgtgct gacccagagc   420
ccggcgaccc tgagcctgag cccggcgaa cgcgcgaccc tgagctgccg cgcgagccag   480
agcattagcg attatctgca ttggtatcag cagaaaccgg gccaggcgcc gcgcctgctg   540
atttattatg cgagccagag cattaccggc attccgcgc gctttagcgg cagcggcagc   600
ggcaccgatt ttaccctgac cattagcagc ctggaaccg aagattttgc ggtgtattat   660
tgccagaacg gccatagctt tccgccgacc tttggcggcg gcaccaaagt ggaaattaaa   720

SEQ ID NO: 3             moltype = AA   length = 118
FEATURE                  Location/Qualifiers
source                   1..118
                         mol_type = protein
                         organism = Homo sapiens
SEQUENCE: 3
QVQLVQSGAE VKKPGSSVKV SCKASGYTFT SYVMHWVRQA PGQGLEWMGY IIPYNDATKY    60
AQKFQGRVTI TADKSTSTAY MELSSLRSED TAVYYCARYN YDGYFDVWGQ GTLVTVSS    118

SEQ ID NO: 4             moltype = AA   length = 15
FEATURE                  Location/Qualifiers
source                   1..15
                         mol_type = protein
                         organism = synthetic construct
SEQUENCE: 4
GGGGSGGGGS GGGGS                                                     15

SEQ ID NO: 5             moltype = AA   length = 107
FEATURE                  Location/Qualifiers
source                   1..107
                         mol_type = protein
                         organism = Homo sapiens
SEQUENCE: 5
EIVLTQSPAT LSLSPGERAT LSCRASQSIS DYLHWYQQKP GQAPRLLIYY ASQSITGIPA    60
RFSGSGSGTD FTLTISSLEP EDFAVYYCQN GHSFPPTFGG GTKVEIK                 107

SEQ ID NO: 6             moltype = AA   length = 240
FEATURE                  Location/Qualifiers
source                   1..240
                         mol_type = protein
                         organism = Homo sapiens
SEQUENCE: 6
QVQLVQSGAE VKKPGSSVKV SCKASGYTFT SYVMHWVRQA PGQGLEWMGY IIPYNDATKY    60
AQKFQGRVTI TADKSTSTAY MELSSLRSED TAVYYCARYN YDGYFDVWGQ GTLVTVSSGG   120
GGSGGGGSGG GGSEIVLTQS PATLSLSPGE RATLSCRASQ SISDYLHWYQ QKPGQAPRLL   180
IYYASQSITG IPARFSGSGS GTDFTLTISS LEPEDFAVYY CQNGHSFPPT FGGGTKVEIK   240

SEQ ID NO: 7             moltype = DNA   length = 63
FEATURE                  Location/Qualifiers
source                   1..63
                         mol_type = other DNA
                         organism = Homo sapiens
```

```
SEQUENCE: 7
atggccttac cagtgaccgc cttgctcctg ccgctggcct tgctgctcca cgccgccagg    60
ccg                                                                  63

SEQ ID NO: 8              moltype = AA   length = 21
FEATURE                   Location/Qualifiers
source                    1..21
                          mol_type = protein
                          organism = Homo sapiens
SEQUENCE: 8
MALPVTALLL PLALLLHAAR P                                              21

SEQ ID NO: 9              moltype = DNA  length = 141
FEATURE                   Location/Qualifiers
source                    1..141
                          mol_type = other DNA
                          organism = Homo sapiens
SEQUENCE: 9
aagcccacca cgacgccagc gccgcgacca ccaacaccgg cgcccaccat cgcgtcgcag    60
cccctgtccc tgcgcccaga ggcgagccgg ccagcggcgg ggggcgcagt gcacacgagg   120
gggctggact cgccagtga t                                              141

SEQ ID NO: 10             moltype = AA   length = 47
FEATURE                   Location/Qualifiers
source                    1..47
                          mol_type = protein
                          organism = Homo sapiens
SEQUENCE: 10
KPTTTPAPRP PTPAPTIASQ PLSLRPEASR PAAGGAVHTR GLDFASD                  47

SEQ ID NO: 11             moltype = DNA  length = 81
FEATURE                   Location/Qualifiers
source                    1..81
                          mol_type = other DNA
                          organism = Homo sapiens
SEQUENCE: 11
ttttgggtgc tggtggtggt tggtggagtc ctggcttgct atagcttgct agtaacagtg    60
gcctttatta ttttctgggt g                                              81

SEQ ID NO: 12             moltype = AA   length = 27
FEATURE                   Location/Qualifiers
source                    1..27
                          mol_type = protein
                          organism = Homo sapiens
SEQUENCE: 12
FWVLVVVGGV LACYSLLVTV AFIIFWV                                        27

SEQ ID NO: 13             moltype = DNA  length = 123
FEATURE                   Location/Qualifiers
source                    1..123
                          mol_type = other DNA
                          organism = Homo sapiens
SEQUENCE: 13
aggagtaaga ggagcaggct cctgcacagt gactacatga acatgactcc ccgccgcccc    60
gggcccaccg gcaagcatta ccagccctat gccccaccac gcgacttcgc agcctatcgc   120
tcc                                                                 123

SEQ ID NO: 14             moltype = AA   length = 41
FEATURE                   Location/Qualifiers
source                    1..41
                          mol_type = protein
                          organism = Homo sapiens
SEQUENCE: 14
RSKRSRLLHS DYMNMTPRRP GPTRKHYQPY APPRDFAAYR S                        41

SEQ ID NO: 15             moltype = DNA  length = 345
FEATURE                   Location/Qualifiers
source                    1..345
                          mol_type = other DNA
                          organism = Homo sapiens
SEQUENCE: 15
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatgggggg aaagccgcag agaaggaaga accctcagga aggcctgtac   180
aatgaactgc agaaagataa gatggcggag gcctacagtg agattgggat gaaaggcgag   240
cgccggaggg gcaaggggca cgatggcctt taccagggtc tcagtacagc caccaaggac   300
acctacgacg cccttcacat gcaggccctg ccccctcgct aatag                   345

SEQ ID NO: 16             moltype = AA   length = 113
```

```
FEATURE                 Location/Qualifiers
source                  1..113
                        mol_type = protein
                        organism = Homo sapiens
SEQUENCE: 16
RVKFSRSADA PAYQQGQNQL YNELNLGRRE EYDVLDKRRG RDPEMGGKPQ RRKNPQEGLY  60
NELQKDKMAE AYSEIGMKGE RRRGKGHDGL YQGLSTATKD TYDALHMQAL PPR         113

SEQ ID NO: 17           moltype = AA  length = 495
FEATURE                 Location/Qualifiers
source                  1..495
                        mol_type = protein
                        organism = Homo sapiens
SEQUENCE: 17
MALPVTALLL PLALLLHAAR PASQVQLVQS GAEVKKPGSS VKVSCKASGY TFTSYVMHWV  60
RQAPGQGLEW MGYIIPYNDA TKYAQKFQGR VTITADKSTS TAYMELSSLR SEDTAVYYCA  120
RYNYDGYFDV WGQGTLVTVS SGGGGSGGGG SGGGGSEIVL TQSPATLSLS PGERATLSCR  180
ASQSISDYLH WYQQKPGQAP RLLIYYASQS ITGIPARFSG SGSGTDFTLT ISSLEPEDFA  240
VYYCQNGHSF PPTFGGGTKV EIKLEKPTTT PAPRPPTPAP TIASQPLSLR PEASRPAAGG  300
AVHTRGLDFA SDKPFWVLVV VGGVLACYSL LVTVAFIIFW VRSKRSRLLH SDYMNMTPRR  360
PGPTRKHYQP YAPPRDFAAY RSRVKFSRSA DAPAYQQGQN QLYNELNLGR REEYDVLDKR  420
RGRDPEMGGK PQRRKNPQEG LYNELQKDKM AEAYSEIGMK GERRRGKGHD GLYQGLSTAT  480
KDTYDALHMQ ALPPR                                                  495

SEQ ID NO: 18           moltype = DNA  length = 126
FEATURE                 Location/Qualifiers
source                  1..126
                        mol_type = other DNA
                        organism = Homo sapiens
SEQUENCE: 18
aaacggggca gaaagaaact cctgtatata ttcaaacaac catttatgag accagtacaa  60
actactcaag aggaagatgg ctgtagctgc cgatttccag aagaagaaga aggaggatgt  120
gaactg                                                            126

SEQ ID NO: 19           moltype = AA  length = 42
FEATURE                 Location/Qualifiers
source                  1..42
                        mol_type = protein
                        organism = Homo sapiens
SEQUENCE: 19
KRGRKKLLYI FKQPFMRPVQ TTQEEDGCSC RFPEEEEGGC EL                     42

SEQ ID NO: 20           moltype = AA  length = 496
FEATURE                 Location/Qualifiers
source                  1..496
                        mol_type = protein
                        organism = Homo sapiens
SEQUENCE: 20
MALPVTALLL PLALLLHAAR PASQVQLVQS GAEVKKPGSS VKVSCKASGY TFTSYVMHWV  60
RQAPGQGLEW MGYIIPYNDA TKYAQKFQGR VTITADKSTS TAYMELSSLR SEDTAVYYCA  120
RYNYDGYFDV WGQGTLVTVS SGGGGSGGGG SGGGGSEIVL TQSPATLSLS PGERATLSCR  180
ASQSISDYLH WYQQKPGQAP RLLIYYASQS ITGIPARFSG SGSGTDFTLT ISSLEPEDFA  240
VYYCQNGHSF PPTFGGGTKV EIKLEKPTTT PAPRPPTPAP TIASQPLSLR PEASRPAAGG  300
AVHTRGLDFA SDKPFWVLVV VGGVLACYSL LVTVAFIIFW VKRGRKKLLY IFKQPFMRPV  360
QTTQEEDGCS CRFPEEEEGG CELRVKFSRS ADAPAYQQGQ NQLYNELNLG RREEYDVLDK  420
RRGRDPEMGG KPQRRKNPQE GLYNELQKDK MAEAYSEIGM KGERRRGKGH DGLYQGLSTA  480
TKDTYDALHM QALPPR                                                 496
```